(12) United States Patent
Furst et al.

(10) Patent No.: US 8,808,618 B2
(45) Date of Patent: *Aug. 19, 2014

(54) PROCESS FOR FORMING AN IMPROVED METAL ALLOY STENT

(75) Inventors: Joseph G. Furst, Lyndhurst, OH (US);
Udayan Patel, San Jose, CA (US);
Raymond W. Buckman, Jr., Pittsburgh, PA (US)

(73) Assignee: Icon Medical Corp., Altanta, GA (US)

( * ) Notice: Subject to any disclaimer, the term of this patent is extended or adjusted under 35 U.S.C. 154(b) by 597 days.

This patent is subject to a terminal disclaimer.

(21) Appl. No.: 12/429,341

(22) Filed: Apr. 24, 2009

(65) Prior Publication Data

US 2009/0200177 A1    Aug. 13, 2009

Related U.S. Application Data

(63) Continuation of application No. 11/635,158, filed on Dec. 1, 2006, now Pat. No. 7,540,995, which is a continuation-in-part of application No. 11/343,104, filed on Jan. 30, 2006, now Pat. No. 7,540,994, which is a continuation-in-part of application No. 11/282,461, filed on Nov. 18, 2005, now Pat. No. 7,452,502, said application No. 11/343,104 is a continuation-in-part of application No. 11/282,376, filed on Nov. 18, 2005, now Pat. No. 7,452,501.

(60) Provisional application No. 60/694,891, filed on Jun. 29, 2005, provisional application No. 60/658,226, filed on Mar. 3, 2005, provisional application No. 60/694,881, filed on Jun. 29, 2005, provisional application No. 60/739,688, filed on Nov. 23, 2005.

(51) Int. Cl.
*B22F 3/24*    (2006.01)

(52) U.S. Cl.
USPC ............................. 419/28; 419/29; 623/1.15

(58) Field of Classification Search
USPC ...................................... 419/28, 29; 613/1.15
IPC ............... B22F 5/106; C22F 1/18; C22C 27/00
See application file for complete search history.

(56) References Cited

U.S. PATENT DOCUMENTS

| | | |
|---|---|---|
| 3,170,234 A | 2/1965 | Tarr |
| 3,964,482 A | 6/1976 | Gerstel |
| 4,043,344 A | 8/1977 | Landi et al. |
| 4,733,665 A | 3/1988 | Palmaz |

(Continued)

FOREIGN PATENT DOCUMENTS

| | | |
|---|---|---|
| CA | 2172187 | 6/2001 |
| EP | 0433011 A1 | 6/1991 |

(Continued)

OTHER PUBLICATIONS

Metals handbook Desk Edition, 2$^{nd}$ Edition. Copyright 1998 by ASM Intl.

(Continued)

*Primary Examiner* — Weiping Zhu
(74) *Attorney, Agent, or Firm* — Fay Sharpe LLP

(57) ABSTRACT

A method and process for at least partially forming a medical device that is at least partially formed of a novel metal alloy which improves the physical properties of the medical device.

35 Claims, 2 Drawing Sheets

(56) References Cited

U.S. PATENT DOCUMENTS

| | | |
|---|---|---|
| 4,739,762 A | 4/1988 | Palmaz |
| 4,776,337 A | 10/1988 | Palmaz |
| 4,841,068 A | 6/1989 | Fujikawa et al. |
| 4,888,389 A | 12/1989 | Kennedy et al. |
| 4,942,204 A | 7/1990 | Kennedy |
| 5,024,671 A | 6/1991 | Tu et al. |
| 5,037,392 A | 8/1991 | Hillstead |
| 5,051,272 A | 9/1991 | Hermes et al. |
| 5,059,166 A | 10/1991 | Fischell et al. |
| 5,059,205 A | 10/1991 | El-Nounov et al. |
| 5,067,491 A | 11/1991 | Taylor, II et al. |
| 5,073,381 A | 12/1991 | Ivan et al. |
| 5,091,205 A | 2/1992 | Fan |
| 5,102,417 A | 4/1992 | Palmaz |
| 5,108,424 A | 4/1992 | Hoffman, Jr. et al. |
| 5,116,318 A | 5/1992 | Hillstead |
| 5,180,366 A | 1/1993 | Woods |
| 5,185,408 A | 2/1993 | Tang et al. |
| 5,195,984 A | 3/1993 | Schatz |
| 5,197,977 A | 3/1993 | Hoffman, Jr. et al. |
| 5,226,909 A | 7/1993 | Evans et al. |
| 5,246,452 A | 9/1993 | Sinnot |
| 5,252,288 A * | 10/1993 | Yamamoto et al. .............. 419/28 |
| 5,263,349 A | 11/1993 | Felix et al. |
| 5,283,257 A | 2/1994 | Gregory et al. |
| 5,304,121 A | 4/1994 | Sahatjian |
| 5,306,250 A | 4/1994 | March et al. |
| 5,316,023 A | 5/1994 | Palmaz |
| 5,344,402 A | 9/1994 | Crocker |
| 5,344,426 A | 9/1994 | Lau et al. |
| 5,370,681 A | 12/1994 | Herweck et al. |
| 5,372,661 A | 12/1994 | Felix et al. |
| 5,383,927 A | 1/1995 | Degoicoechea et al. |
| 5,383,928 A | 1/1995 | Scott et al. |
| 5,417,981 A | 5/1995 | Endo et al. |
| 5,437,744 A | 8/1995 | Carlen |
| 5,443,498 A | 8/1995 | Fontaine |
| 5,449,382 A | 9/1995 | Dayton |
| 5,462,575 A | 10/1995 | Del Corso |
| 5,464,650 A | 11/1995 | Berg et al. |
| 5,500,013 A | 3/1996 | Buscemi et al. |
| 5,516,781 A | 5/1996 | Morris et al. |
| 5,531,195 A * | 7/1996 | Onoda et al. ................... 277/442 |
| 5,545,208 A | 8/1996 | Wolff et al. |
| 5,556,754 A | 9/1996 | Singer |
| 5,563,056 A | 10/1996 | Swan et al. |
| 5,563,146 A | 10/1996 | Morris et al. |
| 5,571,170 A | 11/1996 | Palmaz |
| 5,578,075 A | 11/1996 | Dayton |
| 5,578,645 A | 11/1996 | Askanazi |
| 5,605,696 A | 2/1997 | Eury |
| 5,609,629 A | 3/1997 | Fearnot et al. |
| 5,616,608 A | 4/1997 | Kinsella et al. |
| 5,624,411 A | 4/1997 | Tuch |
| 5,628,787 A | 5/1997 | Mayer |
| 5,632,840 A | 5/1997 | Campbell |
| 5,649,977 A | 7/1997 | Campbell |
| 5,665,728 A | 9/1997 | Morris et al. |
| 5,674,242 A | 10/1997 | Phan et al. |
| 5,679,400 A | 10/1997 | Tuch |
| 5,695,516 A | 12/1997 | Fischell et al. |
| 5,697,971 A | 12/1997 | Fischell et al. |
| 5,716,981 A | 2/1998 | Hunter et al. |
| 5,725,572 A | 3/1998 | Lam et al. |
| 5,733,303 A | 3/1998 | Israel et al. |
| 5,733,925 A | 3/1998 | Kunz et al. |
| 5,735,871 A | 4/1998 | Sgro |
| 5,755,770 A | 5/1998 | Ravenscroft |
| 5,755,781 A | 5/1998 | Jayaraman |
| 5,772,864 A | 6/1998 | Møller et al. |
| 5,776,183 A | 7/1998 | Kanesaka et al. |
| 5,800,511 A | 9/1998 | Mayer |
| 5,807,944 A | 9/1998 | Hirt et al. |
| 5,811,447 A | 9/1998 | Kunz et al. |
| 5,824,045 A | 10/1998 | Alt |
| 5,824,046 A | 10/1998 | Smith et al. |
| 5,824,049 A | 10/1998 | Ragheb et al. |
| 5,824,077 A | 10/1998 | Mayer |
| 5,837,313 A | 11/1998 | Ding et al. |
| 5,843,172 A | 12/1998 | Yan |
| 5,849,368 A | 12/1998 | Hostettler et al. |
| 5,853,419 A | 12/1998 | Imran |
| 5,861,027 A | 1/1999 | Trapp |
| 5,873,904 A | 2/1999 | Ragheb et al. |
| 5,879,370 A | 3/1999 | Fischell et al. |
| 5,891,191 A | 4/1999 | Stinson |
| 5,911,732 A | 6/1999 | Hojeibane |
| 5,916,263 A | 6/1999 | Goicoechea et al. |
| 5,916,585 A | 6/1999 | Cook |
| 5,919,570 A | 7/1999 | Hostettler et al. |
| 5,922,020 A | 7/1999 | Klein et al. |
| 5,951,585 A | 9/1999 | Cathcart et al. |
| 5,957,930 A | 9/1999 | Vrba |
| 5,962,620 A | 10/1999 | Reich et al. |
| 5,964,798 A | 10/1999 | Imran |
| 5,968,091 A | 10/1999 | Pinchuk et al. |
| 5,981,568 A | 11/1999 | Kunz et al. |
| 5,993,545 A | 11/1999 | Lupton |
| 5,993,972 A | 11/1999 | Reich et al. |
| 6,007,573 A | 12/1999 | Wallace et al. |
| 6,039,920 A | 3/2000 | Koch |
| 6,059,810 A | 5/2000 | Brown et al. |
| 6,066,325 A | 5/2000 | Wallace |
| 6,074,659 A | 6/2000 | Kunz et al. |
| 6,093,520 A | 7/2000 | Vladimirsky |
| 6,096,070 A | 8/2000 | Ragheb et al. |
| 6,099,561 A | 8/2000 | Alt |
| 6,102,979 A | 8/2000 | Bianco et al. |
| 6,120,536 A | 9/2000 | Ding et al. |
| 6,120,847 A | 9/2000 | Yang et al. |
| 6,123,712 A | 9/2000 | DiCaprio et al. |
| 6,137,060 A | 10/2000 | Avellanet |
| 6,146,358 A | 11/2000 | Rowe |
| 6,156,062 A | 12/2000 | McGuinness |
| 6,156,373 A | 12/2000 | Zhong et al. |
| 6,162,247 A | 12/2000 | Weadock et al. |
| 6,171,609 B1 | 1/2001 | Kunz |
| 6,190,406 B1 | 2/2001 | Duerig et al. |
| 6,200,337 B1 | 3/2001 | Moriuchi et al. |
| 6,200,589 B1 | 3/2001 | Kennedy et al. |
| 6,200,960 B1 | 3/2001 | Khachigian |
| 6,203,569 B1 | 3/2001 | Wijay |
| 6,206,910 B1 | 3/2001 | Berry et al. |
| 6,206,916 B1 | 3/2001 | Furst |
| 6,221,099 B1 | 4/2001 | Andersen et al. |
| 6,238,491 B1 | 5/2001 | Davidson et al. |
| 6,240,616 B1 | 6/2001 | Yan |
| 6,245,537 B1 | 6/2001 | Williams et al. |
| 6,253,443 B1 | 7/2001 | Johnson |
| 6,254,632 B1 | 7/2001 | Wu et al. |
| 6,258,121 B1 | 7/2001 | Yang et al. |
| 6,267,987 B1 | 7/2001 | Park et al. |
| 6,268,390 B1 | 7/2001 | Kunz |
| 6,273,908 B1 | 8/2001 | Ndondo-Lay |
| 6,273,913 B1 | 8/2001 | Wright et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,421 B1 | 10/2001 | Kunz et al. |
| 6,322,847 B1 | 11/2001 | Zhong et al. |
| 6,334,856 B1 | 1/2002 | Allen et al. |
| 6,335,029 B1 | 1/2002 | Kamath et al. |
| 6,346,133 B1 | 2/2002 | Narasimhan et al. |
| 6,356,600 B1 | 3/2002 | Kirsteins et al. |
| 6,358,556 B1 | 3/2002 | Ding et al. |
| 6,358,989 B1 | 3/2002 | Kunz et al. |
| 6,365,171 B1 | 4/2002 | Kennedy et al. |
| 6,365,616 B1 | 4/2002 | Kohn et al. |
| 6,368,658 B1 | 4/2002 | Schwarz et al. |
| 6,369,065 B1 | 4/2002 | Chatelain et al. |
| 6,379,379 B1 | 4/2002 | Wang |
| 6,379,380 B1 | 4/2002 | Satz |
| 6,379,381 B1 | 4/2002 | Hossainy et al. |
| 6,391,052 B2 | 5/2002 | Buirge et al. |

(56) References Cited

U.S. PATENT DOCUMENTS

| | | |
|---|---|---|
| 6,398,863 B1 | 6/2002 | Okinaka et al. |
| 6,399,144 B2 | 6/2002 | Ding et al. |
| 6,419,692 B1 | 7/2002 | Yang et al. |
| 6,436,133 B1 | 8/2002 | Furst et al. |
| 6,440,460 B1 | 8/2002 | Gurny et al. |
| 6,485,502 B2 | 11/2002 | Don Michael et al. |
| 6,488,702 B1 | 12/2002 | Besselink |
| 6,491,938 B2 | 12/2002 | Kunz et al. |
| 6,515,009 B1 | 2/2003 | Kunz et al. |
| 6,517,571 B1 | 2/2003 | Brauker et al. |
| 6,527,802 B1 | 3/2003 | Mayer |
| 6,528,584 B2 | 3/2003 | Kennedy et al. |
| 6,530,951 B1 | 3/2003 | Bates et al. |
| 6,533,949 B1 | 3/2003 | Yeshurun et al. |
| 6,545,097 B2 | 4/2003 | Pinchuk et al. |
| 6,555,157 B1 | 4/2003 | Hossainy |
| 6,555,619 B1 | 4/2003 | Kennedy et al. |
| 6,558,361 B1 | 5/2003 | Yeshurun |
| 6,569,195 B2 | 5/2003 | Yang et al. |
| 6,569,441 B2 | 5/2003 | Kunz et al. |
| 6,583,251 B1 | 6/2003 | Chaikof et al. |
| 6,585,764 B2 | 7/2003 | Wright et al. |
| 6,596,411 B2 | 7/2003 | Feng et al. |
| 6,599,275 B1 | 7/2003 | Fischer, Jr. |
| 6,599,928 B2 | 7/2003 | Kunz et al. |
| 6,607,598 B2 | 8/2003 | Schwarz et al. |
| 6,623,521 B2 | 9/2003 | Steinke et al. |
| 6,624,138 B1 | 9/2003 | Sung et al. |
| 6,638,301 B1 | 10/2003 | Chandrasekaran et al. |
| 6,641,611 B2 | 11/2003 | Jayaraman |
| 6,652,575 B2 | 11/2003 | Wang |
| 6,656,506 B1 | 12/2003 | Wu et al. |
| 6,656,966 B2 | 12/2003 | Garvey et al. |
| 6,663,881 B2 | 12/2003 | Kunz et al. |
| 6,669,502 B1 | 12/2003 | Bernhart et al. |
| 6,669,718 B2 | 12/2003 | Besselink |
| 6,695,833 B1 | 2/2004 | Frantzen |
| 6,702,849 B1 | 3/2004 | Dutta et al. |
| 6,709,379 B1 | 3/2004 | Brandau et al. |
| 6,720,350 B2 | 4/2004 | Kunz et al. |
| 6,723,120 B2 * | 4/2004 | Yan ............................... 623/1.15 |
| 6,726,923 B2 | 4/2004 | Lyer et al. |
| 6,730,064 B2 | 5/2004 | Ragheb et al. |
| 6,730,349 B2 | 5/2004 | Schwarz et al. |
| 6,730,699 B2 | 5/2004 | Li et al. |
| 6,734,194 B2 | 5/2004 | End et al. |
| 6,743,805 B2 | 6/2004 | End et al. |
| 6,749,554 B1 | 6/2004 | Snow et al. |
| 6,749,629 B1 | 6/2004 | Hong et al. |
| 6,753,071 B1 | 6/2004 | Pacetti |
| 6,759,431 B2 | 7/2004 | Hunter et al. |
| 6,764,505 B1 | 7/2004 | Hossainy et al. |
| 6,767,360 B1 | 7/2004 | Alt et al. |
| 6,770,729 B2 | 8/2004 | Van Antwerp |
| 6,774,278 B1 | 8/2004 | Ragheb et al. |
| 6,780,849 B2 | 8/2004 | Herrmann et al. |
| 6,783,793 B1 | 8/2004 | Hossainy et al. |
| 6,790,218 B2 | 9/2004 | Jayaraman |
| 6,790,372 B2 | 9/2004 | Roy |
| 6,808,536 B2 | 10/2004 | Wright et al. |
| 6,814,049 B2 | 11/2004 | Vogel et al. |
| 6,830,638 B2 | 12/2004 | Boylan et al. |
| 6,861,406 B2 | 3/2005 | Mascarenhas |
| 6,865,810 B2 | 3/2005 | Stinson |
| 6,887,851 B2 | 5/2005 | Mascarenhas |
| 6,920,677 B2 | 7/2005 | Dolan et al. |
| 6,924,087 B2 | 8/2005 | Yeshurun |
| 6,997,946 B2 | 2/2006 | Girton et al. |
| 7,135,038 B1 | 11/2006 | Limon |
| 7,226,467 B2 | 6/2007 | Lucatero et al. |
| 7,540,995 B2 | 6/2009 | Furst et al. |
| 2001/0013166 A1 | 8/2001 | Yan |
| 2001/0014717 A1 | 8/2001 | Hossainy et al. |
| 2001/0032014 A1 | 10/2001 | Yang et al. |
| 2002/0004101 A1 | 1/2002 | Ding et al. |
| 2002/0013275 A1 | 1/2002 | Kunz et al. |
| 2002/0032414 A1 | 3/2002 | Ragheb et al. |
| 2002/0038146 A1 | 3/2002 | Harry |
| 2002/0051730 A1 | 5/2002 | Bodnar et al. |
| 2002/0054900 A1 | 5/2002 | Kamath et al. |
| 2002/0071902 A1 | 6/2002 | Ding et al. |
| 2002/0082679 A1 | 6/2002 | Sirhan et al. |
| 2002/0091433 A1 | 7/2002 | Ding et al. |
| 2002/0098278 A1 | 7/2002 | Bates |
| 2002/0123801 A1 | 9/2002 | Pacetti et al. |
| 2002/0142974 A1 | 10/2002 | Kohn et al. |
| 2002/0155737 A1 | 10/2002 | Roy |
| 2002/0193865 A1 | 12/2002 | Radisch |
| 2002/0198593 A1 | 12/2002 | Gomez et al. |
| 2003/0003220 A1 | 1/2003 | Zhong et al. |
| 2003/0014102 A1 | 1/2003 | Hong et al. |
| 2003/0026840 A1 | 2/2003 | Plank et al. |
| 2003/0028243 A1 | 2/2003 | Bates et al. |
| 2003/0028244 A1 | 2/2003 | Bates et al. |
| 2003/0036794 A1 | 2/2003 | Ragheb et al. |
| 2003/0040790 A1 | 2/2003 | Furst |
| 2003/0044596 A1 | 3/2003 | Lazarov et al. |
| 2003/0064098 A1 | 4/2003 | Kararli et al. |
| 2003/0077200 A1 | 4/2003 | Craig |
| 2003/0083646 A1 | 5/2003 | Sirhan et al. |
| 2003/0093141 A1 | 5/2003 | Dimatteo et al. |
| 2003/0099712 A1 | 5/2003 | Jayaraman |
| 2003/0100499 A1 | 5/2003 | Epstein |
| 2003/0105511 A1 | 6/2003 | Welsh et al. |
| 2003/0181972 A1 | 9/2003 | Jansen et al. |
| 2003/0199969 A1 | 10/2003 | Steinke et al. |
| 2003/0216534 A1 | 11/2003 | Chaikof et al. |
| 2003/0228364 A1 | 12/2003 | Nathan |
| 2003/0229390 A1 | 12/2003 | Ashton |
| 2003/0229392 A1 | 12/2003 | Wong |
| 2003/0229393 A1 | 12/2003 | Kutryk et al. |
| 2004/0000046 A1 | 1/2004 | Stinson |
| 2004/0047909 A1 | 3/2004 | Ragheb et al. |
| 2004/0049261 A1 | 3/2004 | Xu |
| 2004/0049265 A1 | 3/2004 | Ding |
| 2004/0072105 A1 | 4/2004 | Yeshurun |
| 2004/0073291 A1 | 4/2004 | Brown |
| 2004/0086674 A1 | 5/2004 | Holman |
| 2004/0093076 A1 | 5/2004 | White |
| 2004/0093077 A1 | 5/2004 | White |
| 2004/0098014 A1 | 5/2004 | Flugelman |
| 2004/0133271 A1 | 7/2004 | Jang |
| 2004/0143317 A1 | 7/2004 | Stinson |
| 2004/0176834 A1 | 9/2004 | Brown et al. |
| 2004/0193247 A1 | 9/2004 | Besselink |
| 2004/0208985 A1 | 10/2004 | Rowan et al. |
| 2004/0219223 A1 | 11/2004 | Kunz |
| 2004/0230290 A1 | 11/2004 | Weber |
| 2004/0243225 A1 | 12/2004 | Ragheb et al. |
| 2004/0254608 A1 | 12/2004 | Huitema et al. |
| 2004/0265615 A1 | 12/2004 | Kodas |
| 2005/0015136 A1 | 1/2005 | Ikeuchi et al. |
| 2005/0029223 A1 | 2/2005 | Yeshurun |
| 2005/0044687 A1 * | 3/2005 | Matsuguchi et al. .......... 29/455.1 |
| 2005/0092507 A1 | 5/2005 | Marshall |
| 2005/0107870 A1 | 5/2005 | Wang et al. |
| 2005/0131522 A1 | 6/2005 | Stinson |
| 2005/0150096 A1 | 7/2005 | Stinson |
| 2005/0165358 A1 | 7/2005 | Yeshurun |
| 2005/0182482 A1 | 8/2005 | Wang |
| 2005/0209566 A1 | 9/2005 | Yeshurun |
| 2005/0216075 A1 | 9/2005 | Wang |
| 2005/0238522 A1 | 10/2005 | Leonhardt et al. |
| 2006/0020322 A1 | 1/2006 | Leynov et al. |
| 2006/0051404 A1 | 3/2006 | Yeshurun |
| 2006/0136051 A1 | 6/2006 | Furst et al. |
| 2006/0153729 A1 * | 7/2006 | Stinson et al. ................ 420/426 |
| 2006/0200224 A1 | 9/2006 | Furst |
| 2006/0200225 A1 | 9/2006 | Furst |
| 2006/0249556 A1 | 11/2006 | Subramanian et al. |
| 2006/0264914 A1 | 11/2006 | Furst |
| 2007/0003753 A1 | 1/2007 | Asgari |

(56) References Cited

U.S. PATENT DOCUMENTS

| | | |
|---|---|---|
| 2007/0005126 A1 | 1/2007 | Tischler |
| 2007/0077163 A1 | 4/2007 | Furst |
| 2008/0051881 A1 | 2/2008 | Feng et al. |

FOREIGN PATENT DOCUMENTS

| | | |
|---|---|---|
| EP | 0 608 817 | 8/1994 |
| EP | 734721 | 2/1996 |
| EP | 0 700 685 | 3/1996 |
| EP | 714640 | 6/1996 |
| EP | 0 756 853 | 2/1997 |
| EP | 756853 | 2/1997 |
| EP | 0 770 694 | 5/1997 |
| EP | 0836839 A2 | 4/1998 |
| EP | 0 875 218 | 11/1998 |
| EP | 1 046 722 | 10/2000 |
| EP | 1184007 | 3/2002 |
| JP | 8-131532 | 5/1996 |
| JP | 2002-172159 | 6/2002 |
| JP | 2003-290360 | 1/2003 |
| JP | 2003-512098 | 4/2003 |
| JP | 2004-097810 | 4/2004 |
| JP | 2004-532696 A | 10/2004 |
| JP | 2004-534148 | 11/2004 |
| JP | 2000-516486 | 12/2012 |
| SU | 263 888 | 2/1970 |
| SU | 333 209 | 3/1972 |
| SU | 333209 | 3/1972 |
| SU | 489 801 | 10/1975 |
| WO | WO 93/16176 | 8/1993 |
| WO | WO 93/16206 | 8/1993 |
| WO | WO 93/19803 | 10/1993 |
| WO | WO 94/07529 | 4/1994 |
| WO | WO 94/16706 | 8/1994 |
| WO | WO 94/26291 | 11/1994 |
| WO | WO 95/30384 | 11/1995 |
| WO | WO 96/25176 | 8/1996 |
| WO | WO 97/10011 | 3/1997 |
| WO | WO-98/05270 | 2/1998 |
| WO | WO 98/17331 | 4/1998 |
| WO | WO 98/43618 | 10/1998 |
| WO | WO 99/18998 | 4/1999 |
| WO | WO 99/38458 | 8/1999 |
| WO | WO 99/49907 | 10/1999 |
| WO | WO 99/56663 | 11/1999 |
| WO | WO 00/12175 | 3/2000 |
| WO | WO 01/01957 | 1/2001 |
| WO | WO-01/15632 | 3/2001 |
| WO | WO 01/17577 | 3/2001 |
| WO | WO 01/41678 | 6/2001 |
| WO | WO 01/45763 | 6/2001 |
| WO | WO 01/45787 | 6/2001 |
| WO | WO 01/97964 | 12/2001 |
| WO | WO 02/078763 A1 | 10/2002 |
| WO | WO 02/078764 | 10/2002 |
| WO | WO-02/100298 | 12/2002 |
| WO | WO 2004/003240 | 1/2004 |
| WO | WO 2004/019822 | 3/2004 |
| WO | WO 2004/022122 | 3/2004 |
| WO | WO 2008/008291 | 1/2008 |
| WO | WO 2008/008529 | 1/2008 |

OTHER PUBLICATIONS

Dangas G., *Management of restenosis after Coronary Intervention*, Am Heart J. Aug. 1996;132(2 Pt 1):428-36.

Feyter et al., Reference Chart Derived From Post-Stent-Implantation Intravascular Ultrasound Predictors of 6-Month Expected Restenosis on Quantitative Coronary Angiography, Univ. Hosp., Rotterdam, Netherlands, rec'd Dec. 22, 1998, revised Jul. 7, 1999, accepted Jul. 12, 1999.

Forster W. et al., *Influence of Cardiovascular Drugs on Platelet Aggregation*, Adv Myocardiol. 1983;4:539-47.

Galassi et al., Abstract, "A randomized Comparison of Trapidil (triazolopyrimidine), a Platelet-Derived Growth Factor Antagonist, Versus Aspirin in Prevention of Angiographic Restenosis After Coronary Artery Palmaz-Schatz Stent Implantation", Catheter Cardiovasc Interv. Feb. 1999;46(2):162-8.

Lee et al., *Controlled Growth Factor Release from Synthetic Extracellular Matrices*, Nature, vol. 408, Dec. 21/28, 2000.

Liu et al., *Abstract of Trapidil in Preventing Restenosis After Balloon Angioplasty in the Ather Osclerotic Rabbit*, 3d Circulation 1990 81: 1089-1093.

Liu et al., *Trapidil in Preventing Restenosis After Balloon Angioplasty in the Atherosclerotic Rabbit*, Circulation, vol. 81, No. 3, Mar. 1990.

Mani et al., Coronary Stents: A Materials Perspective, Biomaterials, vol. 28, (2007), pp. 1689-1710.

Maresta et al., Abstract of *The Trapidil Restenosis Trial (STARC study): Background, Methods and Clinical Characteristics of the Patient Population*, Clin Trials Metaanal. Apr. 1994;29(1):31-40.

Maresta et al., Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, Circulation, Dec. 1994; 90: 2710-2715.

Matsuda, 2002, "Device-Directed Therapeutic Drug Delivery Systems", Journal of Controlled Release, vol. 78:125-131.

Matsuno et al., Abstract of *Fast and Reproducible Vascular Neointima Formation in the Hamster Carotid Artery: Effects of Trapidil and Captopril*, Thromb Haemost. Dec. 1995;74(6):1591-6.

Ohnishi et al., Abstract of *Pharmacological Properties of Trapidil: Comparison with Other Coronary Vasodilators*, Nippon Yakurigaku Zasshi. Sep. 1980; 76(6):495-503.

Ohnishi, et al., Abstract of *Effects of Trapidil on Thromboxane A2-induced Aggregation of Platelets, Ischemic Changes in Heart and Biosynthesis of Thromboxane A2*, Prostaglandins Med. Mar. 1981;6(3):269-81.

Okamoto et al., Abstract of *Effects of Trapidil (Triazolopyrimidine), a Platelet-Derived Growth Factor Antagonist, in Preventing Restenosis After Percutaneous Transluminal Coronary Angioplasty*, Am Heart J. Jun. 1992; 123(6):1439-44.

Poon, et al., *Trapidil Inhibits Monocyte Chernoattractant Protein-1 and macrophage Accumulation After Balloon Arterial Injury in Rabbits*, Lab Invest. 1999; 79:1369-1375.

Regar et al., 2001. Stent development and local drug delivery. British Medical Bulletin, vol. 59:277-248.

Richardson, et al., *Polymeric System for Dual Growth Factor Delivery*, Nature Biotechnology, vol. 19, Nov. 2001.

Serruys et al., *Results of a Meta-Analysis of Trapidil, a PDGF Inhibitor □'A Sufficient Reason for a Second Look to the Pharmacological Approach to Restenosis*, J Invasive Cardiol. Oct. 1997;9(8):505-512.

Serruys, P.W., et al., *The TRAPIST study—A multicentre randomized placebo controlled clinical trial of trapidil for prevention of restenosis after coronary stenting, measured by 3-D intravascular ultrasound*, on behalf of the TRAPIST investigators, European Heart Journal (2001) 22, 1938-1947, doi:10.1053/euhj.2001.2627, available online at http://www.idealibrary.com.

Shea et al., *DNA Delivery from Polymer Matrices for Tissue Engineering*, Nature.Biotechnology, vol. 17, Jun. 1999.

Sonnenblick, et al., "Progress in Cardiovascular Disease", Sep./Oct. 1996.

Suzuki et al., Abstract of *Antithrombotic Activity and the Mechanism of Action of Trapidil (Rocornal)*, Prostaglandins Leukot Med. Dec. 1982;9(6):685-95.

Terres, et al., *New Aspects in Antithrombotic Therapy—Platelet Inhibitors*, Feb. 1996;21(1):1-11.

Tiell, J.L., et al., Abstract of *Suppression of Fibroblast Proliferation in Vitro and of Myointimal Hyperplasia in Vivo by the Triazolopyrimidine, Trapidil*, Artery, 1983;12(1):33-50.

USCI, PE Plus Peripheral Balloon Dilatation Catheter, USCI Division, C.R. Bard, Inc., Billerica, MA. 012821, U.S. (date not available).

(56) References Cited

OTHER PUBLICATIONS

Refractory Metals Forum: Rhenium and Its Alloys, B.D. Bryskin.

The Effect of Annealing Practice on the Structure and Mechanical Properties of P/M MO—47.5% Re Alloy, John A. Shields, Jr. CLIMAX Specialty Metals, Cleveland, OH 44117.

Delute Mo-Re Alloys—A Critical Evaluation of Thier Comparative Mechanical Properties, J. Watsworth, T.T. Nieg, and J.J. Stephens.

Technology Status of Molybdenum and Tungsten Alloys, W.D. Klopp, Materials Consultant, 1542 Mendelssohn Dr., Westlake, OH 44145.

The Alloys of Rhenium with Molybdenum or with Tungsten and Having Good High Temperature Properties, G.A. Geach and J.E. Hughes.

Behavior of Tungsten, Molybdenum, and Alloys under Unusual Heating Conditions, Ralf Eck, Hubert Bildstein, Fritz Simader, Roland Stickler, Josef Tinzl.

Rhenium and Molybdenum/Tungsten Based Alloys: An Overview of Database, Boris D. Bryskin and Jan C. Carlen.

Mechanical Properties of Mo-Re Alloys at Different Test Temperatures, A.V. Abramyan, N.N. Morgunova, S.A. Golovaneko, and N.I. Kazakova.

Needles, Sutures and Knots, Part III; Specific Suture Materials Al Sherbeeny,M., MD, vol. 1, Jul. 2004.

Microsystems for Drug and Gene Delivery, Michael L. Reed, Senior Member, IEEE & WHYE-KEI LYE, Member, IEEE.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

A New Method for the Estimation for the Absorption Time of Bioabsorbable Polymers in the Body, D.C.tunc, M. Gockbora and P.Higham/ Stryker Howmedica Osteonics, Advanced Technology Group, Mahwa, NJ 07430 USA.

Synthesis and comparative biodegradability studies of three poly(alkylene succinate)s. D. Bikiaris, G. Papageorgiou, D. Achilias, Laboratory of Organic Chemical Technology, Dept. of Chemistry, Aristotle University of Thessaloniki, GR-541 24, Thessaloniki, Macedonia, Greece.

International Search Report—Sep. 20, 2007.

A.J. Mueller, et al., Evaluation of Oxide Dispersion Strengthened (ODS) Molybdenum and Molybdenum-Rhenium Alloys, B-T-3148 (1999), p. 1-18.

Leonhardt et al., "Investigation of Mechanical Properties and Microstructure of Various Molybdenum-Rhenium Alloys", AIP Conference Proceedings, vol. 458, p. 685, 1999.

Freund et al., "Stress-Rupture Strength and Creep Behaviour on Molybdenum-Rhenium Alloys", TMS 129$^{th}$ Annual Meeting & Exhibtion, Mar. 12-16, 2000.

\* cited by examiner

PROCESS FOR FORMING AN IMPROVED METAL ALLOY STENT

The present invention is a continuation of U.S. patent application Ser. No. 11/635,158 filed Dec. 1, 2006, which in turn is a continuation-in-part of U.S. patent application Ser. No. 11/343,104 filed Jan. 30, 2006, which in turn is a continuation-in-part of U.S. patent application Ser. No. 11/282,461 filed Nov. 18, 2005 entitled "Metal Alloy for a Stent" which claims priority on U.S. Provisional Application Ser. No. 60/694,891 filed Jun. 29, 2005 entitled "Improved Metal Alloys for Medical Devices," all of which are incorporated herein by reference.

The present invention is also a continuation of U.S. patent application Ser. No. 11/635,158 filed Dec. 1, 2006, which in turn is a continuation-in-part of U.S. patent application Ser. No. 11/343,104 filed Jan. 30, 2006, which in turn is a continuation-in-part of U.S. patent application Ser. No. 11/282,376 filed Nov. 18, 2005 entitled "Metal Alloy for a Stent," which is incorporated herein by reference.

The present invention is also a continuation of U.S. patent application Ser. No. 11/635,158 filed Dec. 1, 2006, which in turn is a continuation-in-part of U.S. patent application Ser. No. 11/343,104 filed Jan. 30, 2006, which in turn claims priority on U.S. Provisional Application Ser. Nos. 60/658,226 filed Mar. 3, 2005 entitled "Improved Metal Alloys for Medical Devices"; 60/694,881 filed Jun. 29, 2005 entitled "Improved Metal Alloys for Medical Devices"; and 60/739,688 filed Nov. 23, 2005 entitled "Process for Forming an Improved Metal Alloy Stent," all of which are incorporated herein by reference.

The invention relates generally to medical devices, and particularly to a method and process for forming a medical device that is at least partially formed of a novel metal alloy, and more particularly to a method and process for forming a stent that is at least partially formed of a novel molybdenum and rhenium metal alloy.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy. One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent can contribute directly to the success rate of the device. These physical attributes include radiopacity, hoop strength, radial force, thickness of the metal, dimensions of the metal and the like. Cobalt and chromium alloys and stainless steel are commonly used to form stents. These materials are commonly used since such materials have a known history of safety, effectiveness and biocompatibility. These materials however have limited physical performance characteristics as to size, strength, weight, bendability, biostability and radiopacity.

The present invention is generally directed to a method and process for manufacturing and producing a medical device, and more particularly directed to a method and process for manufacturing and producing a stent that is at least partially formed of a novel metal alloy.

SUMMARY OF THE INVENTION

The present invention is generally directed to a medical device that is at least partially made of a novel metal alloy having improved properties as compared to past medical devices. The novel metal alloy used to at least partially form the medical device improves one or more properties (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, etc.) of such medical device. These one or more improved physical properties of the novel metal alloy can be achieved in the medical device without having to increase the bulk, volume and/or weight of the medical device, and in some instances these improved physical properties can be obtained even when the volume, bulk and/or weight of the medical device is reduced as compared to medical devices that are at least partially formed from traditional stainless steel or cobalt and chromium alloy materials. The novel metal alloy that is used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improve the recoil properties of the medical device, 11) improve the friction coefficient of the medical device, 12) improve the heat sensitivity properties of the medical device, 13) improve the biostability and/or biocompatibility properties of the medical device, and/or 14) enable smaller, thinner and/or lighter weight medical devices to be made. The medical device generally includes one or more materials that impart the desired properties to the medical device so as to withstand the manufacturing processes that are needed to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, etc.

In one non-limiting aspect of the present invention, a medical device that can include the novel metal alloy is a stent for use in a body passageway; however, it can be appreciated that other types of medical devices could be at least partially formed from the novel metal alloy. As used herein, the term "body passageway" is defined to be any passageway or cavity in a living organism (e.g., bile duct, bronchial tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, interventional procedures, and any combinations thereof. For vascular applications, the term "body passageway" primarily refers to blood vessels and chambers in the heart. The stent can be an expandable stent that is expandable by a balloon and/or other means.

The stent can have many shapes and forms. Such shapes can include, but are not limited to, stents disclosed in U.S. Pat. Nos. 6,206,916 and 6,436,133; and all the prior art cited in these patents. These various designs and configurations of stents in such patents are incorporated herein by reference.

In another and/or alternative non-limiting aspect of the present invention, the medical device is generally designed to include at least about 25 weight percent of the novel metal alloy; however, this is not required. In one non-limiting embodiment of the invention, the medical device includes at least about 40 weight percent of the novel metal alloy. In another and/or alternative non-limiting embodiment of the invention, the medical device includes at least about 50 weight percent of the novel metal alloy. In still another and/or alternative non-limiting embodiment of the invention, the medical device includes at least about 60 weight percent of the novel metal alloy. In yet another and/or alternative non-limiting embodiment of the invention, the medical device includes at least about 70 weight percent of the novel metal alloy. In still yet another and/or alternative non-limiting embodiment of the invention, the medical device includes at least about 85 weight percent of the novel metal alloy. In a further and/or alternative non-limiting embodiment of the invention, the medical device includes at least about 90 weight percent of the novel metal alloy. In still a further and/or alternative non-limiting embodiment of the invention, the medical device includes at least about 95 weight percent of the novel metal alloy. In yet a further and/or alternative non-limiting embodiment of the invention, the medical device includes about 100 weight percent of the novel metal alloy.

In still another and/or alternative non-limiting aspect of the present invention, the novel metal alloy that is used to form all or part of the medical device 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the novel metal alloy of the present invention may be clad, metal sprayed, plated and/or formed onto another metal, or another metal or metal alloy may be plated, metal sprayed, clad and/or formed onto the novel metal alloy when forming all or a portion of a medical device.

In yet another and/or alternative non-limiting aspect of the present invention, the novel metal alloy that is used to form all or a portion of the medical device includes rhenium and molybdenum. The novel alloy can include one or more other metals such as, but not limited to, calcium, chromium, cobalt, copper, gold, iron, lead, magnesium, nickel, niobium, platinum, rare earth metals, silver, tantalum, titanium, tungsten, yttrium, zinc, zirconium, and/or alloys thereof.

In still another and/or alternative non-limiting aspect of the present invention, the novel metal alloy that is used to form all or a portion of the medical device is a novel metal alloy that includes at least about 90 weight percent molybdenum and rhenium. In one non-limiting composition, the content of molybdenum and rhenium in the novel metal alloy is at least about 95 weight percent. In another and/or alternative non-limiting composition, the content of molybdenum and rhenium in the novel metal alloy is at least about 97 weight percent. In still another and/or alternative non-limiting composition, the content of molybdenum and rhenium in the novel metal alloy is at least about 98 weight percent. In yet another and/or alternative non-limiting composition, the content of molybdenum and rhenium in the novel metal alloy is at least about 99 weight percent. In still yet another and/or alternative non-limiting composition, the content of molybdenum and rhenium in the novel metal alloy is at least about 99.5 weight percent. In a further one non-limiting composition, the content of molybdenum and rhenium in the novel metal alloy is at least about 99.9 weight percent. In still a further and/or alternative non-limiting composition, the content of molybdenum and rhenium in the novel metal alloy is at least about 99.95 weight percent. In yet a further and/or alternative non-limiting composition, the content of molybdenum and rhenium in the novel metal alloy is at least about 99.99 weight percent. As can be appreciated, other weight percentages of the rhenium and molybdenum content of the novel metal alloy can be used. In one non-limiting composition, the purity level of the novel metal alloy is such so as to produce a solid solution of the novel metal alloy. A solid solution or homogeneous solution is defined as a metal alloy that includes two or more primary metals and the combined weight percent of the primary metals is at least about 95 weight percent, typically at least about 99 weight percent, more typically at least about 99.5 weight percent, even more typically at least about 99.8 weight percent, and still even more typically at least about 99.9 weight percent. A primary metal is a metal component of the metal alloy that is not a metal impurity. A solid solution of a novel metal alloy that includes rhenium and molybdenum as the primary metals is an alloy that includes at least about 95-99 weight percent rhenium and molybdenum. It is believed that a purity level of less than 95 weight percent molybdenum and rhenium adversely affects one or more physical properties of the metal alloy that are useful or desired in forming and/or using a medical device. In one embodiment of the invention, the rhenium content of the novel metal alloy in accordance with the present invention is at least about 40 weight percent. In one non-limiting composition, the rhenium content of the novel metal alloy is at least about 45 weight percent. In still another and/or alternative non-limiting composition, the rhenium content of the novel metal alloy is about 45-50 weight percent. In yet another and/or alternative non-limiting composition, the rhenium content of the novel metal alloy is about 47-48 weight percent. In still yet another and/or alternative non-limiting composition, the rhenium content of the novel metal alloy is about 47.6-49.5 weight percent. As can be appreciated, other weight percentages of the rhenium content of the novel metal alloy can be used. In another and/or alternative embodiment of the invention, the molybdenum content of the novel metal alloy in accordance with the present invention is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and/or alternative non-limiting composition, the molybdenum content of the novel metal alloy is about 50-56 weight percent. As can be appreciated, other weight percentages of the molybdenum content of the novel metal alloy can be used.

In still yet another and/or alternative non-limiting aspect of the present invention, the novel metal alloy that is used to form all or a portion of the medical device is a novel metal alloy that includes at least about 90 weight percent molybdenum and rhenium, and at least one additional metal which includes titanium, yttrium, and/or zirconium. The addition of controlled amounts of titanium, yttrium, and/or zirconium to the molybdenum and rhenium alloy has been found to form a metal alloy that has improved physical properties over a metal alloy that principally includes molybdenum and rhenium. For instance, the addition of controlled amounts of titanium, yttrium, and/or zirconium to the molybdenum and rhenium alloy can result in 1) an increase in yield strength of the alloy as compared to a metal alloy that principally includes molybdenum and rhenium, 2) an increase in tensile elongation of the alloy as compared to a metal alloy that principally includes molybdenum and rhenium, 3) an increase in ductility of the alloy as compared to a metal alloy that principally includes molybdenum and rhenium, 4) a reduction in grain size of the alloy as compared to a metal alloy that principally includes molybdenum and rhenium, 5) a reduction in the amount of free carbon, oxygen and/or nitrogen in the alloy as compared to a metal alloy that principally includes molybdenum and rhenium, and/or 6) a reduction in the tendency of the alloy to form micro-cracks during the forming of the alloy into a medical device as compared to the forming of a medical device from a metal alloy that principally includes molybdenum and rhenium. In one non-limiting composition, the content of molybdenum and rhenium and the at least one additional metal in the novel metal alloy is at least about 90 weight percent. In another and/or alternative non-limiting composition, the content of molybdenum and rhenium and the at least one additional metal in the novel metal alloy is at least about 95 weight percent. In still another and/or alternative non-limiting composition, the content of molybdenum and rhenium and the at least one additional metal in the novel metal alloy is at least about 98 weight percent. In yet another and/or alternative non-limiting composition, the content of molybdenum and rhenium and the at least one additional metal in the novel metal alloy is at least about 99 weight percent. In still yet another and/or alternative non-limiting composition, the content of molybdenum and rhenium and the at least one additional metal in the novel metal alloy is at least about 99.5 weight percent. In a further one non-limiting composition, the content of molybdenum and rhenium and the at least one additional metal in the novel metal alloy is at least about 99.9 weight percent. In still a further and/or alternative non-limiting composition, the content of molybdenum and rhenium and the at least one additional metal in the novel metal alloy is at least about 99.95 weight percent. In yet a further and/or alternative non-limiting composition, the content of molybdenum and rhenium and the at least one additional metal in the novel metal alloy is at least about 99.99 weight percent. As can be appreciated, other weight percentages of the content of molybdenum and rhenium and the at least one additional metal in the novel metal alloy can be used. In one non-limiting composition, the purity level of the novel metal alloy is such so as to produce a solid solution of a rhenium and molybdenum and the at least one additional metal. A solid solution of a novel metal alloy that includes rhenium and molybdenum and the at least one additional metal of titanium, yttrium and/or zirconium as the primary metals is an alloy that includes at least about 95-99 weight percent rhenium and molybdenum and the at least one additional metal. It is believed that a purity level of less than 95 weight percent molybdenum and rhenium and the at least one additional metal adversely affects one or more physical properties of the metal alloy that are useful or desired in forming and/or using a medical device. In one embodiment of the invention, the rhenium content of the novel metal alloy in accordance with the present invention is at least about 40 weight percent. In one non-limiting composition, the rhenium content of the novel metal alloy is at least about 45 weight percent. In still another and/or alternative non-limiting composition, the rhenium content of the novel metal alloy is about 45-50 weight percent. In yet another and/or alternative non-limiting composition, the rhenium content of the novel metal alloy is about 47-48 weight percent. As can be appreciated, other weight percentages of the rhenium content of the novel metal alloy can be used. In another and/or alternative embodiment of the invention, the molybdenum content of the novel metal alloy is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and/or alternative non-limiting composition, the molybdenum content of the novel metal alloy is about 50-56 weight percent. As can be appreciated, other weight percentages of the molybdenum content of the novel metal alloy can be used. The combined content of titanium, yttrium and zirconium in the novel metal alloy is less than about 5 weight percent, typically no more than about 1 weight percent, and more typically no more than about 0.5 weight percent. A higher weight percent content of titanium, yttrium and/or zirconium in the novel metal alloy can begin to adversely affect the brittleness of the novel metal alloy. When titanium is included in the novel metal alloy, the titanium content is typically less than about 1 weight percent, more typically less than about 0.6 weight percent, even more typically about 0.05-0.5 weight percent, still even more typically about 0.1-0.5 weight percent. As can be appreciated, other weight percentages of the titanium content of the novel metal alloy can be used. When zirconium is included in the novel metal alloy, the zirconium content is typically less than about 0.5 weight percent, more typically less than about 0.3 weight percent, even more typically about 0.01-0.25 weight percent, still even more typically about 0.05-0.25 weight percent. As can be appreciated, other weight percentages of the zirconium content of the novel metal alloy can be used. When titanium and zirconium are included in the novel metal alloy, the weight ratio of titanium to zirconium is about 1-10:1, typically about 1.5-5:1, and more typically about 1.75-2.5:1. When yttrium is included in the novel metal alloy, the yttrium content is typically less than about 0.3 weight percent, more typically less than about 0.2 weight percent, and even more typically about 0.01-0.1 weight percent. As can be appreciated, other weight percentages of the yttrium content of the novel metal alloy can be used. The inclusion of titanium, yttrium and/or zirconium in the novel metal alloy is believed to result in a reduction of oxygen trapped in the solid solution of the novel metal alloy. The reduction of trapped oxygen enables the formation of a smaller grain size in the novel metal alloy and/or an increase in the ductility of the novel metal alloy. The reduction of trapped oxygen in the novel metal alloy can also increase the yield strength of the novel metal alloy as compared to alloys of only molybdenum and rhenium (i.e., 2-10% increase). The inclusion of titanium, yttrium and/or zirconium in the novel metal alloy is also believed to cause a reduction in the trapped free carbon in the novel metal alloy. The inclusion of titanium, yttrium and/or zirconium in the novel metal alloy is believed to form carbides with the free carbon in the novel metal alloy. This carbide formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The inclusion of titanium, yttrium and/or zirconium in the novel metal alloy is also believed to cause a reduction in the trapped free nitrogen in the novel metal alloy. The inclusion of titanium, yttrium and/or zirconium in the novel metal alloy is believed to form carbo-nitrides with the free carbon and free nitrogen in the novel metal alloy. This carbo-nitride formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The reduction in the amount of free carbon, oxygen and/or nitrogen in the novel metal alloy is also believed to increase the density of the novel metal alloy (i.e., 1-5% increase). The formation of carbides, carbo-nitrides, and/or oxides in the novel metal alloy results in the formation of dispersed second phase particles in the novel metal alloy, thereby facilitating in the formation of small grain sizes in the metal alloy.

In still another and/or alternative non-limiting aspect of the present invention, the novel metal alloy includes less than about 5 weight percent other metals and/or impurities. A high purity level of the novel metal alloy results in the formation of a more homogeneous alloy, which in turn results in a more uniform density throughout the novel metal alloy, and also results in the desired yield and ultimate tensile strengths of the novel metal alloy. The density of the novel metal alloy is generally at least about 12 gm/cc, and typically at least about 13-13.5 gm/cc. This substantially uniform high density of the novel metal alloy significantly improves the radiopacity of the novel metal alloy. In one non-limiting composition, the novel metal alloy includes less than about 1 weight percent other metals and/or impurities. In another and/or alternative non-limiting composition, the novel metal alloy includes less than about 0.5 weight percent other metals and/or impurities. In still another and/or alternative non-limiting composition, the novel metal alloy includes less than about 0.4 weight percent other metals and/or impurities. In yet another and/or alternative non-limiting composition, the novel metal alloy includes less than about 0.2 weight percent other metals and/or impurities. In still yet another and/or alternative non-limiting composition, the novel metal alloy includes less than about 0.1 weight percent other metals and/or impurities. In a further and/or alternative non-limiting composition, the novel metal alloy includes less than about 0.05 weight percent other metals and/or impurities. In still a further and/or alternative non-limiting composition, the novel metal alloy includes less than about 0.02 weight percent other metals and/or impurities. In yet a further and/or alternative non-limiting composition, the novel metal alloy includes less than about 0.01 weight percent other metals and/or impurities. As can be appreciated, other weight percentages of the amount of other metals and/or impurities in the novel metal alloy can exist.

In yet another and/or alternative non-limiting aspect of the present invention, the novel metal alloy includes a certain amount of carbon and oxygen. These two elements have been found to affect the forming properties and brittleness of the novel metal alloy. The controlled atomic ratio of carbon and oxygen in the novel metal alloy also can be used to minimize the tendency of the novel metal alloy to form micro-cracks during the forming of the novel alloy into a medical device, and/or during the use and/or expansion of the medical device in a body passageway. In one non-limiting embodiment of the invention, the novel metal alloy includes up to about 200 ppm carbon and up to about 150 ppm oxygen. Higher carbon and oxygen contents in the novel metal alloy are believed to adversely affect one or more physical properties of the metal alloy that are useful or desired in forming and/or using a medical device. In one non-limiting formulation, the novel metal alloy includes up to about 150 ppm carbon. In still another and/or alternative non-limiting formulation, the novel metal alloy includes up to about 100 ppm carbon. In yet another and/or alternative non-limiting formulation, the novel metal alloy includes less than about 50 ppm carbon. In still yet another and/or alternative non-limiting formulation, the novel metal alloy includes up to about 100 ppm oxygen. In a further and/or alternative non-limiting formulation, the novel metal alloy includes up to about 75 ppm oxygen. In still a further and/or alternative non-limiting formulation, the novel metal alloy includes up to about 50 ppm oxygen. In yet a further and/or alternative non-limiting formulation, the novel metal alloy includes up to about 30 ppm oxygen. In still yet a further and/or alternative non-limiting formulation, the novel metal alloy includes less than about 20 ppm oxygen. In yet a further and/or alternative non-limiting formulation, the novel metal alloy includes less than about 10 ppm oxygen. As can be appreciated, other amounts of carbon and/or oxygen in the novel metal alloy can exist. In another and/or alternative non-limiting embodiment of the invention, the carbon to oxygen atomic ratio in the novel metal alloy is generally at least about 2:1 (i.e., weight ratio of about 1.5:1). The control of the atomic ratio of carbon to oxygen in the novel metal alloy allows for the redistribution of oxygen in the metal alloy so as to minimize the tendency of micro-cracking in the novel metal alloy during the forming of the novel alloy into a medical device, and/or during the use and/or expansion of the medical device in a body passageway. When the carbon to oxygen atomic ratio falls below 2-2.5:1 (i.e., weight ratio of about 1.5-1.88:1), the degree of elongation of the novel metal alloy decreases and the incidence of micro-cracking increases, thus adversely affecting one or more physical properties of the metal alloy that are useful or desired in forming and/or using the medical device. In one non-limiting formulation, the carbon to oxygen atomic ratio in the novel metal alloy is generally at least about 2.5:1 (i.e., weight ratio of about 1.88:1). In another and/or alternative non-limiting formulation, the carbon to oxygen atomic ratio in the novel metal alloy is generally at least about 3:1 (i.e., weight ratio of about 2.25:1). In still another and/or alternative non-limiting formulation, the carbon to oxygen atomic ratio in the novel metal alloy is generally at least about 4:1 (i.e., weight ratio of about 3:1). In yet another and/or alternative non-limiting formulation, the carbon to oxygen atomic ratio in the novel metal alloy is generally at least about 5:1 (i.e., weight ratio of about 3.75:1). In still yet another and/or alternative non-limiting formulation, the carbon to oxygen atomic ratio in the novel metal alloy is generally about 2.5-50:1 (i.e., weight ratio of about 1.88-37.54:1). In a further and/or alternative non-limiting formulation, the carbon to oxygen atomic ratio in the novel metal alloy is generally about 2.5-20:1 (i.e., weight ratio of about 1.88-15:1). In still a further and/or alternative non-limiting formulation, the carbon to oxygen atomic ratio in the novel metal alloy is generally about 2.5-10:1 (i.e., weight ratio of about 1.88-7.5:1). In yet a further and/or alternative non-limiting formulation, the carbon to oxygen atomic ratio in the novel metal alloy is generally about 2.5-5:1 (i.e., weight ratio of about 1.88-3.75:1). As can be appreciated, other atomic ratios of the carbon to oxygen in the novel metal alloy can be used.

In still yet another and/or alternative non-limiting aspect of the present invention, the novel metal alloy includes a controlled amount of nitrogen. Large amounts of nitrogen in the novel metal alloy can adversely affect the ductility of the novel metal alloy. This can in turn adversely affect the elongation properties of the novel metal alloy. A nitrogen content in the novel metal alloy of over 20 ppm can begin to cause the ductility of the novel metal alloy to unacceptably decrease, thus adversely affect one or more physical properties of the metal alloy that are useful or desired in forming and/or using the medical device. In one non-limiting embodiment of the invention, the novel metal alloy includes less than about 30 ppm nitrogen. In one non-limiting formulation, the novel metal alloy includes less than about 25 ppm nitrogen. In still another and/or alternative non-limiting formulation, the novel metal alloy includes less than about 10 ppm nitrogen. In yet another and/or alternative non-limiting formulation, the novel metal alloy includes less than about 5 ppm nitrogen. As can be appreciated, other amounts of nitrogen in the novel metal alloy can exist.

In a further and/or alternative non-limiting aspect of the present invention, the novel metal alloy has several physical properties that positively affect the medical device when at least partially formed of the novel metal alloy. In one non-limiting embodiment of the invention, the average Vickers hardness of the novel metal alloy tube used to form the medical device is generally at least about 234 DHP (i.e., Rockwell A hardness of at least about 60 at 77° F., Rockwell C hardness of at least about 19 at 77° F.). In one non-limiting aspect of this embodiment, the average hardness of the novel metal alloy used to form the medical device is generally at least about 248 DHP (i.e., Rockwell A hardness of at least about 62 at 77° F., Rockwell C hardness of at least about 22 at 77° F.). In another and/or additional non-limiting aspect of this embodiment, the average hardness of the novel metal alloy used to form the medical device is generally about 248-513 DHP (i.e., Rockwell A hardness of about 62-76 at 77° F., Rockwell C hardness of about 22-50 at 77° F.). In still another and/or additional non-limiting aspect of this embodiment, the average hardness of the novel metal alloy used to form the medical device is generally about 272-458 DHP (i.e., Rockwell A hardness of about 64-74 at 77° F., Rockwell C hardness of about 26-46 at 77° F.). In another and/or alternative non-limiting embodiment of the invention, the average ultimate tensile strength of the novel metal alloy used to form the medical device is generally at least about 60 UTS (ksi). In non-limiting aspect of this embodiment, the average ultimate tensile strength of the novel metal alloy used to form the medical device is generally at least about 70 UTS (ksi), typically about 80-320 UTS (ksi), and more typically about 100-310 UTS (ksi). The average ultimate tensile strength of the novel metal alloy will very somewhat when the novel metal alloy is in the form of a tube or a solid wire. When the novel metal alloy is in the form of a tube, the average ultimate tensile strength of the novel metal alloy tube is generally about 80-150 UTS (ksi). When the novel metal alloy is in the form of a solid wire, the average ultimate tensile strength of the novel metal alloy wire is generally about 120-310 UTS (ksi). In still another and/or alternative non-limiting embodiment of the invention, the average yield strength of the novel metal alloy used to form the medical device is at least about 70 ksi. In one non-limiting aspect of this embodiment, the average yield strength of the novel metal alloy used to form the medical device is at least about 80 ksi, and typically about 100-140 (ksi). In yet another and/or alternative non-limiting embodiment of the invention, the average grain size of the novel metal alloy used to form the medical device is no greater than about 5 ASTM (e.g., ASTM E 112-96). The grain size can be as small as about 14-15 ASTM can be achieved; however, the grain size is typically larger than 15 ASTM. The small grain size of the novel metal alloy enables the medical device to have the desired elongation and ductility properties that are useful in enabling the medical device to be formed, crimped and/or expanded. In one non-limiting aspect of this embodiment, the average grain size of the novel metal alloy used to form the medical device is about 5.2-10 ASTM, typically about 5.5-9 ASTM, more typically about 6-9 ASTM, still more typically about 6-9 ASTM, even more typically about 6.6-9 ASTM, and still even more typically about 7-8.5 ASTM. In still yet another and/or alternative non-limiting embodiment of the invention, the average tensile elongation of the novel metal alloy used to form the medical device is at least about 25%. An average tensile elongation of at least 25% for the novel metal alloy is important to enable the medical device to be properly expanded when positioned in the treatment area of a body passageway. A medical device that does not have an average tensile elongation of at least about 25% can form micro-cracks and/or break during the forming, crimping and/or expansion of the medical device. In one non-limiting aspect of this embodiment, the average tensile elongation of the novel metal alloy used to form the medical device is about 25-35%. The unique combination of the rhenium content in the novel metal alloy in combination with achieving the desired purity and composition of the alloy and the desired grain size of the novel metal alloy results in 1) a medical device having the desired high ductility at about room temperature, 2) a medical device having the desired amount of tensile elongation, 3) a homogeneous or solid solution of a metal alloy having high radiopacity, 4) a reduction or prevention of microcrack formation and/or breaking of the metal alloy tube when the metal alloy tube is sized and/or cut to form the medical device, 5) a reduction or prevention of microcrack formation and/or breaking of the medical device when the medical device is crimped onto a balloon and/or other type of medical device for insertion into a body passageway, 6) a reduction or prevention of microcrack formation and/or breaking of the medical device when the medical device is bent and/or expanded in a body passageway, 7) a medical device having the desired ultimate tensile strength and yield strength, 8) a medical device that can have very thin wall thicknesses and still have the desired radial forces needed to retain the body passageway on an open state when the medical device has been expanded, and/or 9) a medical device that exhibits less recoil when the medical device is crimped onto a delivery system and/or expanded in a body passageway.

Several non-limiting examples of the novel metal alloy that can be made in accordance with the present invention are set forth below:

|       | Wt. %     |           |           |
|-------|-----------|-----------|-----------|
| Metal | Ex. 1     | Ex. 2     | Ex. 3     |
| C     | <150 ppm  | <50 ppm   | <50 ppm   |
| Mo    | 51-54%    | 52.5-55.5%| 50.5-52.4%|
| O     | <50 ppm   | <10 ppm   | <10 ppm   |
| N     | <20 ppm   | <10 ppm   | <10 ppm   |
| Re    | 46-49%    | 44.5-47.5%| 47.6-49.5%|

|       | Wt. %     |           |           |           |
|-------|-----------|-----------|-----------|-----------|
| Metal | Ex. 4     | Ex. 5     | Ex. 6     | Ex. 7     |
| C     | ≤50 ppm   | ≤50 ppm   | ≤50 ppm   | ≤50 ppm   |
| Mo    | 51-54%    | 52.5-55.5%| 52-56%    | 52.5-55%  |
| O     | ≤20 ppm   | ≤20 ppm   | ≤10 ppm   | ≤10 ppm   |
| N     | ≤20 ppm   | ≤20 ppm   | ≤10 ppm   | ≤10 ppm   |
| Re    | 46-49%    | 44.5-47.5%| 44-48%    | 45-47.5%  |
| Ti    | ≤0.4%     | ≤0.4%     | 0.2-0.4%  | 0.3-0.4%  |
| Y     | ≤0.1%     | ≤0.1%     | 0-0.08%   | 0.005-0.05%|
| Zr    | ≤0.2%     | ≤0.2%     | 0-0.2%    | 0.1-0.25% |

-continued

| | Wt. % | | | |
|---|---|---|---|---|
| Metal | Ex. 8 | Ex. 9 | Ex. 10 | Ex. 11 |
| C | ≤40 ppm | ≤40 ppm | ≤40 ppm | ≤40 ppm |
| Mo | 50.5-53% | 51.5-54% | 52-55% | 52.5-55% |
| O | ≤15 ppm | ≤15 ppm | ≤15 ppm | ≤10 ppm |
| N | ≤10 ppm | ≤10 ppm | ≤10 ppm | ≤10 ppm |
| Re | 47-49.5% | 46-48.5% | 45-48% | 45-47.5% |
| Ti | 0.1-0.35% | 0% | 0% | 0.1-0.3% |
| Y | 0% | 0.002-0.08% | 0% | 0% |
| Zr | 0% | 0% | 00.1-0.2% | 0.05-0.15% |

| | Wt. % | | | |
|---|---|---|---|---|
| Metal | Ex. 12 | Ex. 13 | Ex. 14 | Ex. 15 |
| C | ≤40 ppm | ≤40 ppm | <150 ppm | <150 ppm |
| Mo | 52-55% | 52.5-55.5% | 50-60% | 50-60% |
| O | ≤10 ppm | ≤10 ppm | ≤100 ppm | ≤100 ppm |
| N | ≤10 ppm | ≤10 ppm | ≤40 ppm | ≤40 ppm |
| Re | 45-49% | 44.5-47.5% | 40-50% | 40-50% |
| Ti | 0.05-0.4% | 0% | 0% | ≤1% |
| Y | 0.005-0.07% | 0.004-0.06% | 0% | ≤0.1% |
| Zr | 0% | 0.1-0.2% | 0% | ≤2% |

| | Wt. % | | | |
|---|---|---|---|---|
| Metal | Ex. 16. | Ex. 17 | Ex. 18 | Ex. 19 |
| C | ≤150 ppm | ≤150 ppm | ≤150 ppm | ≤150 ppm |
| Mo | 50-55% | 52-55.5% | 51-58% | 50-56% |
| O | ≤100 ppm | ≤100 ppm | ≤100 ppm | ≤100 ppm |
| N | ≤40 ppm | ≤20 ppm | ≤20 ppm | ≤20 ppm |
| Re | 45-50% | 44.5-48% | 42-49% | 44-50% |
| Ti | 0% | 0% | 0% | 0% |
| Y | 0% | 0% | 0% | 0% |
| Zr | 0% | 0% | 0% | 0% |

| | Wt. % | | |
|---|---|---|---|
| Metal | Ex. 20 | Ex. 21 | Ex. 22 |
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |
| Ti | 0% | 0% | 0% |
| Y | 0% | 0% | 0% |
| Zr | 0% | 0% | 0% |

| | Wt. % | | |
|---|---|---|---|
| Metal | Ex. 23 | Ex. 24 | Ex. 25 |
| C | ≤150 ppm | ≤150 ppm | ≤150 ppm |
| Mo | 50-60% | 50-60% | 50-55% |
| O | ≤100 ppm | ≤100 ppm | ≤100 ppm |
| N | ≤40 ppm | ≤40 ppm | ≤40 ppm |
| Re | 40-50% | 40-50% | 45-50% |
| Ti | ≤0.5% | ≤0.5% | ≤0.5% |
| Y | ≤0.1% | ≤0.1% | ≤0.1% |
| Zr | ≤0.25% | ≤0.25% | ≤0.25% |

| | Wt. % | | |
|---|---|---|---|
| Metal | Ex. 26 | Ex. 27 | Ex. 28 |
| C | ≤150 ppm | ≤150 ppm | ≤150 ppm |
| Mo | 52-55.5% | 51-58% | 50-56% |
| O | ≤100 ppm | ≤100 ppm | ≤100 ppm |
| N | ≤20 ppm | ≤20 ppm | ≤20 ppm |
| Re | 44.5-48% | 42-49% | 44-50% |
| Ti | ≤0.5% | ≤0.5% | ≤0.5% |
| Y | ≤0.1% | ≤0.1% | ≤0.1% |
| Zr | ≤0.25% | ≤0.25% | ≤0.25% |

In examples 1-3, 14 and 16-22 above, the novel metal alloy is principally formed of rhenium and molybdenum and the content of other metals and/or impurities is less than about 0.1 weight percent of the novel metal alloy, the atomic ratio of carbon to oxygen is about 2.5-10:1 (i.e., weight ratio of about 1.88-7.5:1), the average grain size of the novel metal alloy is about 6-9 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 150-310 UTS (ksi), and an average Vickers hardness of 372-653 (i.e., Rockwell A Hardness of about 70-80 at 77° F., an average Rockwell C Hardness of about 39-58 at 77° F.). In examples 4-13, 15 and 23-28 above, the novel metal alloy is principally formed of rhenium and molybdenum and at least one metal of titanium, yttrium and/or zirconium, and the content of other metals and/or impurities is less than about 0.1 weight percent of the novel metal alloy, the ratio of carbon to oxygen is about 2.5-10:1, the average grain size of the novel metal alloy is about 6-9 ASTM, the tensile elongation of the metal alloy is about 25-35%, the average density of the metal alloy is at least about 13.6 gm/cc, the average yield strength of the metal alloy is at least about 110 (ksi), the average ultimate tensile strength of the metal alloy is about 150-310 UTS (ksi), and an average Vickers hardness of 372-653 (i.e., an average Rockwell A Hardness of about 70-80 at 77° F., an average Rockwell C Hardness of about 39-58 at 77° F.).

In another and/or alternative non-limiting aspect of the present invention, the use of the novel metal alloy in the medical device can increase the strength of the medical device as compared with stainless steel or chromium-cobalt alloys, thus less quantity of novel metal alloy can be used in the medical device to achieve similar strengths as compared to medical devices formed of different metals. As such, the resulting medical device can be made smaller and less bulky by use of the novel metal alloy without sacrificing the strength and durability of the medical device. Such a medical device can have a smaller profile, thus can be inserted in smaller areas, openings and/or passageways. The novel metal alloy also can increase the radial strength of the medical device. For instance, the thickness of the walls of the medical device and/or the wires used to form the medical device can be made thinner and achieve a similar or improved radial strength as compared with thicker walled medical devices formed of stainless steel or cobalt and chromium alloy. The novel metal alloy also can improve stress-strain properties, bendability and flexibility of the medical device, thus increase the life of the medical device. For instance, the medical device can be used in regions that subject the medical device to bending. Due to the improved physical properties of the medical device from the novel metal alloy, the medical device has improved resistance to fracturing in such frequent bending environments. In addition or alternatively, the improved bendability and flexibility of the medical device due to the use of the novel metal alloy can enable the medical device to be more easily inserted into a body passageway. The novel metal alloy can also reduce the degree of recoil during the crimping and/or expansion of the medical device. For example, the medical device better maintains its crimped form and/or better maintains its expanded form after expansion due to the use of the novel metal alloy. As such, when the medical device is to be mounted onto a delivery device when the medical device is crimped, the medical device better maintains its smaller profile during the insertion of the medical device in a body passageway. Also, the medical device better maintains its expanded profile after expansion so as to facilitate in the success of the medical device in the treatment area. In addition to the improved physical properties of the medical device by use of the novel metal alloy, the novel metal alloy has improved radiopaque properties as compared to standard materials such as stainless steel or cobalt-chromium alloy, thus reducing or eliminating the need for using marker materials on the medical device. For instance, the novel metal alloy is believed to at least about 10-20% more radiopaque than stainless steel or cobalt-chromium alloy. Specifically, the novel metal alloy is believed to be at least about 33% more radiopaque than cobalt-chromium alloy and is believed to be at least about 41.5% more radiopaque than stainless steel.

In still yet another and/or alternative non-limiting aspect of the present invention, the medical device that is at least partially formed from the novel metal alloy can be formed by a variety of manufacturing techniques. In one non-limiting embodiment of the invention, the medical device can be formed from a rod or tube of the novel metal alloy. If a solid rod of the novel metal alloy is formed, the rod can be cut or drilled (e.g., gun drilled, EDM, etc.) to form a cavity or passageway partially or fully through the rod. The rod or tube can be cleaned, polished, annealed, drawn, etc. to obtain the desired cross-sectional area or diameter and/or wall thickness of the metal tube. After the metal tube has been formed to the desired cross-sectional area or diameter and wall thickness, the metal tube can be formed into a medical device by a process such as, but not limited to, laser cutting, etching, etc. After the medical device has been formed, the medical device can be cleaned, polished, sterilized, etc. for final processing of the medical device. As can be appreciated, other or additional process steps can be used to at least partially form the medical device from the novel metal alloy.

In a further and/or alternative non-limiting aspect of the present invention, the novel alloy used to at least partially form the medical device is initially formed into a rod or a tube of novel metal alloy. The novel metal alloy rod or tube can be formed by various techniques such as, but not limited to, 1) melting the novel metal alloy and/or metals that form the novel metal alloy (e.g., vacuum arc melting, etc.) and then extruding and/or casting the novel metal alloy into a rod or tube, 2) melting the novel metal alloy and/or metals that form the novel metal alloy, forming a metal strip and then rolling and welding the strip into a tube, or 3) consolidating metal power of the novel metal alloy and/or metal powder of metals that form the novel metal alloy. The rod or tube, however formed, generally has a length of about 48 inches or less; however, longer lengths can be formed. The average outer diameter of the rod or tube is generally less than about 2 inches (i.e., less than about 3.14 sq. in. cross-sectional area), more typically less than about 1 inch outer diameter, and even more typically no more than about 0.5 inch outer diameter; however, larger rod or tube diameter sizes can be formed. In one non-limiting configuration for a tube, the tube has an inner diameter of about 0.31 inch plus or minus about 0.002 inch and an outer diameter of about 0.5 inch plus or minus about 0.002 inch. The wall thickness of the tube is about 0.095 inch plus or minus about 0.002 inch. As can be appreciated, this is just one example of many different sized tubes that can be formed. In one non-limiting process, the rod or tube can be formed from one or more ingots of metal or metal alloy. In one non-limiting process, an arc melting process (e.g., vacuum arc melting process, etc.) can be used to form the one or more ingots. In another non-limiting process, rhenium powder and molybdenum powder can be placed in a crucible (e.g., silica crucible, etc.) and heated under a controlled atmosphere (e.g., vacuum environment, carbon monoxide environment, hydrogen and argon environment, helium, argon, etc.) by an induction melting furnace. It can be appreciated that other or additional processes can be used to form the one or more ingots.

Once the ingots are formed, the metal ingots can be cast, extruded through a die, etc. to form the rod or tube. During an extrusion process, the ingots are generally heated; however, this is not required. A close-fitting rod can be used during the extrusion process to form the tube; however, this is not required. In another and/or additional non-limiting process, the tube of the novel metal alloy can be formed from a strip or sheet of novel metal alloy. The strip or sheet of novel metal alloy can be formed into a tube by rolling the edges of the sheet or strip and then welding together the edges of the sheet or strip. The welding of the edges of the sheet or strip can be accomplished in several ways such as, but not limited to, a) holding the edges together and then e-beam welding the edges together in a vacuum, b) positioning a thin strip of novel metal alloy above and/or below the edges of the rolled strip or sheet to be welded, then welding the one or more strips along the rolled strip or sheet edges, and then grinding off the outer strip, or c) laser welding the edges of the rolled sheet or strip in a vacuum, oxygen reducing atmosphere, or inert atmosphere. In still another and/or additional non-limiting process, the rod or tube of the novel metal alloy is formed by consolidating metal power. In this process, fine particles of molybdenum and rhenium along with any additives are mixed to form a homogenous blend of particles. Typically the average particle size of the metal powders is less than about 200 mesh (e.g., less than 74 microns). A larger average particle size can interfere with the proper mixing of the metal powders and/or adversely affect one or more physical properties of the rod or tube formed from the metal powders. In one non-limiting embodiment, the average particle size of the metal powders is less than about 230 mesh (e.g., less than 63 microns). In another and/or alternative non-limiting embodiment, the average particle size of the metal powders is about 2-63 microns, and more particularly about 5-40 microns. As can be appreciated, smaller average particle sizes can be used. The purity of the metal powders should be selected so that the metal powders contain very low levels of carbon, oxygen and nitrogen. Typically the carbon content of the molybdenum metal powder is less than about 100 ppm, the oxygen content of the molybdenum metal powder is less than about 50 ppm, and the nitrogen content of the molybdenum metal powder is less than about 20 ppm. Typically, the carbon content of the rhenium metal powder is less than about 100 ppm, the oxygen content of the rhenium metal powder is less than about 50 ppm, and the nitrogen content of the rhenium metal powder is less than about 20 ppm. Typically, metal powder having a purity grade of at least 99.9 and more typically at least about 99.95 should be used to obtain the desired purity of the powders of molybdenum and rhenium. When titanium, yttrium and/or zirconium powder is added to the metal powder mixture, the amount of carbon, oxygen and nitrogen in the power should also be minimized. Typically, metal powder having a purity grade of at least 99.8 and more typically at least about 99.9 should be used to obtain the desired purity of the powders of titanium, yttrium and/or zirconium. The blend of metal powder is then pressed together to form a solid solution of the novel metal alloy into a rod or tube. Typically the pressing process is by an isostatic process (i.e., uniform pressure applied from all sides on the metal powder). When the metal powders are pressed together isostatically, cold isostatic pressing (CIP) is typically used to consolidate the metal powders; however, this is not required. The pressing process can be preformed in an inert atmosphere, an oxygen reducing atmosphere (e.g., hydrogen, argon and hydrogen mixture, etc.) and/or under a vacuum; however, this is not required. The average density of the rod or tube that is achieved by pressing together the metal powders is about 80-90% of the final average density of the rod or tube or about 70-96% the minimum theoretical density of the novel metal alloy. Pressing pressures of at least about 300 MPa are generally used. Generally the pressing pressure is about 400-700 MPa; however, other pressures can be used. After the metal powders are pressed together, the pressed metal powders are sintered at high temperature (e.g., 2000-2900° C.) to fuse the metal powders together to form the solid metal rod or tube. The sintering of the consolidated metal powder can be preformed in an oxygen reducing atmosphere (e.g., helium, argon, hydrogen, argon and hydrogen mixture, etc.) and/or under a vacuum; however, this is not required. At the high sintering temperatures, a high hydrogen atmosphere will reduce both the amount of carbon and oxygen in the formed rod or tube. The sintered metal powder generally has an as-sintered average density of about 90-99% the minimum theoretical density of the novel metal alloy. Typically, the sintered rod or tube has a final average density of at least about 12 gm/cc, typically at least about 12.5 gm/cc, and more typically about 13-14 gm/cc. A rod or tube formed by compressed and sintered metal powders typically has an average concentricity deviation that is less than a rod or tube formed by an arc melting and molding process, extrusion process, or a sheet and welding process; however, this is not always the situation. Generally, the average concentricity deviation of the rod or tube that is formed from compressed and sintered metal powders is less than about 20%, typically about 1-18%, and more typically about 1-5%.

In still a further and/or alternative non-limiting aspect of the present invention, when a solid rod of the novel metal alloy is formed, the rod is then formed into a tube prior to reducing the outer cross-sectional area or diameter of the rod. The rod can be formed into a tube by a variety of processes such as, but not limited to, cutting or drilling (e.g., gun drilling, etc.) or by cutting (e.g., EDM, etc.). The cavity or passageway formed in the rod typically is formed fully through the rod; however, this is not required.

In yet a further and/or alternative non-limiting aspect of the present invention, the rod or tube can be cleaned and/or polished after the rod or tube has been form; however, this is not required. Typically the rod or tube is cleaned and/or polished prior to being further processed; however, this is not required. When a rod of the novel metal alloy is formed into a tube, the formed tube is typically cleaned and/or polished prior to being further process; however, this is not required. When the rod or tube is resized and/or annealed as discussed in detail below, the resized and/or annealed rod or tube is typically cleaned and/or polished prior to and/or after each or after a series of resizing and/or annealing processes; however, this is not required. The cleaning and/or polishing of the rod or tube is used to remove impurities and/or contaminants from the surfaces of the rod or tube. Impurities and contaminants can become incorporated into the novel metal alloy during the processing of the rod or tube. The inadvertent incorporation of impurities and contaminants in the rod or tube can result in an undesired amount of carbon, nitrogen and/or oxygen, and/or other impurities in the novel metal alloy. The inclusion of impurities and contaminants in the novel metal alloy can result in premature micro-cracking of the novel metal alloy and/or an adverse affect on one or more physical properties of the novel metal alloy (e.g., decrease in tensile elongation, increased ductility, etc.). The cleaning of the novel metal alloy can be accomplished by a variety of techniques such as, but not limited to, 1) using a solvent (e.g., acetone, methyl alcohol, etc.) and wiping the novel metal alloy with a Kimwipe or other appropriate towel, 2) by at least partially dipping or immersing the novel metal alloy in a solvent and then ultrasonically cleaning the novel metal alloy, and/or 3) by at least partially dipping or immersing the novel metal alloy in a pickling solution. As can be appreciated, the novel metal alloy can be cleaned in other or additional ways. If the novel metal alloy is to be polished, the novel metal alloy is generally polished by use of a polishing solution that typically includes an acid solution; however, this is not required. In one non-limiting example, the polishing solution includes sulfuric acid; however, other or additional acids can be used. In one non-limiting polishing solution, the polishing solution can include by volume 60-95% sulfuric acid and 5-40% de-ionized water (DI water). Typically, the polishing solution that includes an acid will increase in temperature during the making of the solution and/or during the polishing procedure. As such, the polishing solution is typically stirred and/or cooled during making of the solution and/or during the polishing procedure. The temperature of the polishing solution is typically about 20-100° C., and typically greater than about 25° C. One non-limiting polishing technique that can be used is an electro-polishing technique. When an electro-polishing technique is used, a voltage of about 2-30V, and typically about 5-12V is applied to the rod or tube during the polishing process; however, it will be appreciated that other voltages can be used. The time used to polish the novel metal alloy is dependent on both the size of the rod or tube and the amount of material that needs to be removed from the rod or tube. The rod or tube can be processed by use of a two-step polishing process wherein the novel metal alloy piece is at least partially immersed in the polishing solution for a given period (e.g., 0.1-15 minutes, etc.), rinsed (e.g., DI water, etc.) for a short period of time (e.g., 0.02-1 minute, etc.), and then flipped over and at least partially immersed in the solution again for the same or similar duration as the first time; however, this is not required. The novel metal alloy can be rinsed (e.g., DI water, etc.) for a period of time (e.g., 0.01-5 minutes, etc.) before rinsing with a solvent (e.g., acetone, methyl alcohol, etc.); however, this is not required. The novel metal alloy can be dried (e.g., exposure to the atmosphere, maintained in an inert gas environment, etc.) on a clean surface. These polishing procedures can be repeated until the desired amount of polishing of the rod or tube is achieved. The rod or tube can be uniformly electropolished or selectively electropolished. When the rod or tube is selectively electropolished, the selective electropolishing can be used to obtain different surface characteristics of the rod or tube and/or selectively expose one or more regions of the rod or tube; however, this is not required.

In still yet a further and/or alternative non-limiting aspect of the present invention, the rod or tube is resized to the desired dimension of the medical device. In one non-limiting embodiment, the cross-sectional area or diameter of the rod or tube is reduced to a final rod or tube dimension in a single step or by a series of steps. The reduction of the outer cross-sectional area or diameter of the rod may be obtained by either centerless grinding, turning, electropolishing, drawing process etc. During the reduction the tube, the outer tube cross-sectional area or diameter, the inner tube cross-sectional area or diameter and/or wall thickness of the tube are typically reduced; however, this is not required. The outer cross-sectional area or diameter size of the rod or tube is typically reduced by the use of one or more drawing processes. During the drawing process, care should be taken to not form micro-cracks in the rod or tube during the reduction of the rod or tube outer cross-sectional area or diameter. Generally, the rod or tube should not be reduced in cross-sectional area by more about 25% each time the rod or tube is drawn through a reducing mechanism (e.g., a die, etc.). In one non-limiting process step, the rod or tube is reduced in cross-sectional area by about 0.1-20% each time the rod or tube is drawn through a reducing mechanism. In another and/or alternative non-limiting process step, the rod or tube is reduced in cross-sectional area by about 1-15% each time the rod or tube is drawn through a reducing mechanism. In still another and/or alternative non-limiting process step, the rod or tube is reduced in cross-sectional area by about 2-15% each time the rod or tube is drawn through reducing mechanism. In yet another one non-limiting process step, the rod or tube is reduced in cross-sectional area by about 5-10% each time the rod or tube is drawn through reducing mechanism. In another and/or alternative non-limiting embodiment of the invention, the rod or tube of novel metal alloy is drawn through a die to reduce the cross-sectional area of the rod or tube. The tube drawing process is typically a cold drawing process or a plug drawing process through a die. When a cold drawing or mandrel drawing process is used, a lubricant (e.g., molybdenum paste, grease, etc.) is typically coated on the outer surface of the tube and the tube is then drawn though the die. Typically, little or no heat is used during the cold drawing process. After the tube has been drawn through the die, the outer surface of the tube is typically cleaned with a solvent to remove the lubricant so as to limit the amount of impurities that are incorporated in the novel metal alloy. This cold drawing process can be repeated several times until the desired outer cross-sectional area or diameter, inner cross-sectional area or diameter and/or wall thickness of the tube is achieved. A plug drawing process can also or alternatively be used to size the tube. The plug drawing process typically does not use a lubricant during the drawing process. The plug drawing process typically includes a heating step to heat the tube prior and/or during the drawing of the tube through the die. The elimination of the use of a lubricant can reduce the incidence of impurities being introduced into the metal alloy during the drawing process. During the plug drawing process, the tube can be protected from oxygen by use of a vacuum environment, a non-oxygen environment (e.g., hydrogen, argon and hydrogen mixture, nitrogen, nitrogen and hydrogen, etc.) or an inert environment. One non-limiting protective environment includes argon, hydrogen or argon and hydrogen; however, other or additional inert gasses can be used. As indicated above, the rod or tube is typically cleaned after each drawing process to remove impurities and/or other undesired materials from the surface of the rod or tube; however, this is not required. Typically the rod or tube should be shielded from oxygen and nitrogen when the temperature of the rod or tube is increased to above 500° C., and typically above 450° C., and more typically above 400° C. When the rod or tube is heated to temperatures above about 400-500° C., the rod or tube has a tendency to begin form nitrides and/or oxides in the presence of nitrogen and oxygen. In these higher temperature environments, a hydrogen environment, argon and hydrogen environment, etc. is generally used. When the rod or tube is drawn at temperatures below 400-500° C., the tube can be exposed to air with little or no adverse affects; however, an inert or slightly reducing environment is generally more desirable.

In still a further and/or alternative non-limiting aspect of the present invention, the rod or tube during the drawing process can be nitrided. The nitride layer on the rod or tube can function as a lubricating surface during the drawing process to facilitate in the drawing of the rod or tube. The rod or tube is generally nitrided in the presence of nitrogen or a nitrogen mixture (e.g., 97% N-3% H, etc.) for at least about 1 minute at a temperature of at least about 400° C. In one-limiting nitriding process, the rod or tube is heated in the presence of nitrogen or a nitrogen-hydrogen mixture to a temperature of about 400-800° C. for about 1-30 minutes. In one non-limiting embodiment of the invention, the surface of the rod or tube is nitrided prior to at least one drawing step for the rod or tube. In one non-limiting aspect of this embodiment, the surface of the rod or tube is nitrided prior to a plurality of drawing steps. In another non-limiting aspect of this invention, after the rod or tube has been annealed, the rod or tube is nitrided prior to being drawn. In another and/or alternative non-limiting embodiment, the rod or tube is cleaned to remove nitride compounds on the surface of the rod or tube prior to annealing the rod to tube. The nitride compounds can be removed by a variety of steps such as, but not limited to, and grit blasting, polishing, etc. After the rod or tube has been annealed, the rod or tube can be again nitrided prior to one or more drawing steps; however, this is not required. As can be appreciated, the complete outer surface of the tube can be nitrided or a portion of the outer surface of the tube can be nitrided. Nitriding only selected portions of the outer surface of the tube can be used to obtain different surface characteristics of the tube; however, this is not required.

In still yet a further and/or alternative non-limiting aspect of the present invention, the rod or tube is annealed after one or more drawing processes. The metal alloy rod or tube can be annealed after each drawing process or after a plurality of drawing processes. The metal alloy rod or tube is typically annealed prior to about a 60% cross-sectional area size reduction of the metal alloy rod or tube. In other words, the rod or tube should not be reduced in cross-sectional area by more than 60% before being annealed. A too large of a reduction in the cross-sectional area of the metal alloy rod or tube during the drawing process prior to the rod or tube being annealed can result in micro-cracking of the rod or tube. In one non-limiting processing step, the metal alloy rod or tube is annealed prior to about a 50% cross-sectional area size reduction of the metal alloy rod or tube. In another and/or alternative non-limiting processing step, the metal alloy rod or tube is annealed prior to about a 45% cross-sectional area size reduction of the metal alloy rod or tube. In still another and/or alternative non-limiting processing step, the metal alloy rod or tube is annealed prior to about a 1-45% cross-sectional area size reduction of the metal alloy rod or tube. In yet another and/or alternative non-limiting processing step, the metal alloy rod or tube is annealed prior to about a 5-30% cross-sectional area size reduction of the metal alloy rod or tube. In still yet another and/or alternative non-limiting processing step, the metal alloy rod or tube is annealed prior to about a 5-15% cross-sectional area size reduction of the metal alloy rod or tube. When the rod or tube is annealed, the rod or tube is typically heated to a temperature of about 1200-1700° C. for a period of about 2-200 minutes; however, other temperatures and/or times can be used. In one non-limiting processing step, the metal alloy rod or tube is annealed at a temperature of about 1400-1600° C. for about 2-100 minutes. The annealing process typically occurs in an inert environment or an oxygen reducing environment so as to limit the amount of impurities that may embed themselves in the novel metal alloy during the annealing process. One non-limiting oxygen reducing environment that can be used during the annealing process is a hydrogen environment; however, it can be appreciated that a vacuum environment can be used or one or more other or additional gasses can be used to create the oxygen reducing environment. At the annealing temperatures, a hydrogen containing atmosphere can further reduce the amount of oxygen in the rod or tube. The chamber in which the rod or tube is annealed should be substantially free of impurities (e.g., carbon, oxygen, and/or nitrogen) so as to limit the amount of impurities that can embed themselves in the rod or tube during the annealing process. The annealing chamber typically is formed of a material that will not impart impurities to the rod or tube as the rod or tube is being annealed. A non-limiting material that can be used to form the annealing chamber includes, but is not limited to, molybdenum, rhenium, tungsten, molybdenum TZM alloy, ceramic, etc. When the rod or tube is restrained in the annealing chamber, the restraining apparatuses that are used to contact the novel metal alloy rod or tube are typically formed of materials that will not introduce impurities to the novel metal alloy during the processing of the rod or tube. Non-limiting examples of materials that can be used to at least partially form the restraining apparatuses include, but are not limited to, molybdenum, titanium, yttrium, zirconium, rhenium and/or tungsten. In still another and/or alternative non-limiting processing step, the parameters for annealing can be changed as the tube as the cross-sectional area or diameter; and/or wall thickness of the tube are changed. It has been found that good grain size characteristics of the tube can be achieved when the annealing parameters are varied as the parameters of the tube change. In one non-limiting processing arrangement, the annealing temperature of the tube having a wall thickness of greater than about 0.015 inch is generally at least about 1480° C. for a time period of at least about 5 minutes. In another non-limiting processing arrangement, the annealing temperature of the tube having a wall thickness of about 0.008-0.015 inch is generally about 1450-1480° C. for a time period of at least about 5 minutes. In another non-limiting processing arrangement, the annealing temperature of the tube having a wall thickness of less than about 0.008 inch is generally less than about 1450° C. for a time period of at least about 5 minutes. As such, as the wall thickness is reduced, the annealing temperature is correspondingly reduced; however, the times for annealing can be increased. As can be appreciated, the annealing temperatures of the tube can be decreased as the wall thickness decreases, but the annealing times can remain the same or also be reduced as the wall thickness reduces. After each annealing process, the grain size of the metal in the tube should be no greater than 5 ASTM. Grain sizes of 7-14 ASTM can be achieved by the annealing process of the present invention. It is believed that as the annealing temperature is reduced as the wall thickness reduces, small grain sizes can be obtained. The grain size of the metal in the tube should be as uniform as possible. In addition, the sigma phase of the metal in the tube should be as reduced as much as possible. The sigma phase is a spherical, elliptical or tetragonal crystalline shape in the metal alloy. The sigma phase is commonly formed of both rhenium and molybdenum, typically with a larger concentration of rhenium. After the final drawing of the tube, a final annealing of the tube can be done for final strengthening of the tube; however, this is not required. This final annealing process, when used, generally occurs at a temperature of about 1300-1600° C. for at least about 5 minutes; however, other temperatures and/or time periods can be used.

In another and/or alternative non-limiting aspect of the present invention, the rod or tube can be cleaned prior to and/or after being annealed. The cleaning process is designed to remove impurities, lubricants (e.g., nitride compounds, molybdenum paste, grease, etc.) and/or other materials from the surfaces of the rod or tube. Impurities that are on one or more surfaces of the rod or tube can become permanently embedded into the rod or tube during the annealing processes. These imbedded impurities can adversely affect the physical properties of the novel metal alloy as the rod or tube is formed into a medical device, and/or can adversely affect the operation and/or life of the medical device. In one non-limiting embodiment of the invention, the cleaning process includes a delubrication or degreasing process which is typically followed by pickling process; however, this is not required. The delubrication or degreasing process followed by pickling process are typically used when a lubricant has been used on the rod or tube during a drawing process. Lubricants commonly include carbon compounds, nitride compounds, molybdenum paste, and other types of compounds that can adversely affect the novel metal alloy if such compounds and/or elements in such compounds become associated and/or embedded with the novel metal alloy during an annealing process. The delubrication or degreasing process can be accomplished by a variety of techniques such as, but not limited to, 1) using a solvent (e.g., acetone, methyl alcohol, etc.) and wiping the novel metal alloy with a Kimwipe or other appropriate towel, 2) by at least partially dipping or immersing the novel metal alloy in a solvent and then ultrasonically cleaning the novel metal alloy, 3) sand blasting the novel metal alloy, and/or 4) chemical etching the metal alloy. As can be appreciated, the novel metal alloy can be delubricated or degreased in other or additional ways. After the novel metal alloy rod or tube has been delubricated or degreased, the rod or tube can be further cleaned by use of a pickling process; however, this is not required. The pickling process, when used, includes the use of one or more acids to remove impurities from the surface of the rod or tube. Non-limiting examples of acids that can be used as the pickling solution include, but are not limited to, nitric acid, acetic acid, sulfuric acid, hydrochloric acid, and/or hydrofluoric acid. These acids are typically analytical reagent (ACS) grade acids. The acid solution and acid concentration are selected to remove oxides and other impurities on the rod or tube surface without damaging or over etching the surface of the rod or tube. A rod or tube surface that includes a large amount of oxides and/or nitrides typically requires a stronger pickling solution and/or long picking process times. Non-limiting examples of pickling solutions include 1) 25-60% DI water, 30-60% nitric acid, and 2-20% sulfuric acid; 2) 40-75% acetic acid, 10-35% nitric acid, and 1-12% hydrofluoric acid; and 3) 50-100% hydrochloric acid. As can be appreciated, one or more different pickling solutions can be used during the pickling process. During the pickling process, the rod or tube is fully or partially immersed in the pickling solution for a sufficient amount of time to remove the impurities from the surface of the rod or tube. Typically, the time period for pickling is about 2-120 seconds; however, other time periods can be used. After the rod or tube has been pickled, the rod or tube is typically rinsed with a water (e.g., DI water, etc.) and/or a solvent (e.g., acetone, methyl alcohol, etc.) to remove any pickling solution from the rod or tube and then the rod or tube is allowed to dry. The rod or tube may be keep in a protective environment during the rinse and/or drying process to inhibit or prevent oxides from reforming on the surface of the rod or tube prior to the rod or tube being drawn and/or annealed; however, this is not required.

In yet another and/or alternative non-limiting aspect of the present invention, the restraining apparatuses that are used to contact the novel metal alloy rod or tube during an annealing process and/or drawing process are typically formed of materials that will not introduce impurities to the novel metal alloy during the processing of the rod or tube. In one non-limiting embodiment, when the metal alloy rod or tube is exposed to temperatures above 150° C., the materials that contact the novel metal alloy rod or tube during the processing of the rod or tube are typically made from molybdenum, rhenium and/or tungsten. When the novel metal alloy rod or tube is processed at lower temperatures (i.e., 150° C. or less), materials made from Teflon parts can also or alternatively be used.

In still another and/or alternative non-limiting aspect of the present invention, the novel metal alloy rod or tube, after being formed to the desired outer cross-sectional area or diameter, inner cross-sectional area or diameter and/or wall thickness, can be cut and/or etched to at least partially form the desired configuration of the medical device (e.g., stent, etc.). In one non limiting embodiment of the invention, the novel metal alloy rod or tube is at least partially cut by a laser. The laser is typically desired to have a beam strength which can heat the novel metal alloy rod or tube to a temperature of at least about 2200-2300° C. In one non-limiting aspect of this embodiment, a pulsed Nd:YAG neodymium-doped yttrium aluminum garnet ($Nd:Y_3Al_5O_{12}$) or $CO_2$ laser is used to at least partially cut a pattern of medical device out of the novel metal alloy rod or tube. In another and/or alternative non-limiting aspect of this embodiment, the cutting of the novel metal alloy rod or tube by the laser can occur in a vacuum environment, an oxygen reducing environment, or an inert environment; however, this is not required. It has been found that laser cutting of the rod or tube in a non-protected environment can result in impurities being introduced into the cut rod or tube, which introduced impurities can induce microcracking of the rod or tube during the cutting of the rod or tube. One non-limiting oxygen reducing environment includes a combination of argon and hydrogen; however, a vacuum environment, an inert environment, or other or additional gasses can be used to form the oxygen reducing environment. In still another and/or alternative non-limiting aspect of this embodiment, the novel metal alloy rod or tube is stabilized so as to limit or prevent vibration of the rod or tube during the cutting process. The apparatus used to stabilize the rod or tube can be formed of molybdenum, rhenium, tungsten, molybdenum TZM alloy, ceramic, etc. so as to not introduce contaminants to the rod or tube during the cutting process; however, this is not required. Vibrations in the rod or tube during the cutting of the rod or tube can result in the formation of micro-cracks in the rod or tube as the rod or tube is cut. The average amplitude of vibration during the cutting of the rod or tube should be no more than about 150% the wall thickness of the rod or tube. In one non-limiting aspect of this embodiment, the average amplitude of vibration should be no more than about 100% the wall thickness of the rod or tube. In another non-limiting aspect of this embodiment, the average amplitude of vibration should be no more than about 75% the wall thickness of the rod or tube. In still another non-limiting aspect of this embodiment, the average amplitude of vibration should be no more than about 50% the wall thickness of the rod or tube. In yet another non-limiting aspect of this embodiment, the average amplitude of vibration should be no more than about 25% the wall thickness of the rod or tube. In still yet another non-limiting aspect of this embodiment, the average amplitude of vibration should be no more than about 15% the wall thickness of the rod or tube.

In still yet another and/or alternative non-limiting aspect of the present invention, the novel metal alloy rod or tube, after being formed to the desired medical device, can be cleaned, polished, sterilized, nitrided, etc. for final processing of the medical device. In one non-limiting embodiment of the invention, the medical device is electropolished. In one non-limiting aspect of this embodiment, the medical device is cleaned prior to being exposed to the polishing solution; however, this is not required. The cleaning process, when used, can be accomplished by a variety of techniques such as, but not limited to, 1) using a solvent (e.g., acetone, methyl alcohol, etc.) and wiping the medical device with a Kimwipe or other appropriate towel, and/or 2) by at least partially dipping or immersing the medical device in a solvent and then ultrasonically cleaning the medical device. As can be appreciated, the medical device can be cleaned in other or additional ways. In another and/or alternative non-limiting aspect of this embodiment, the polishing solution can include one or more acids. One non-limiting formulation of the polishing solution includes about 10-80 percent by volume sulfuric acid. As can be appreciated, other polishing solution compositions can be used. In still another and/or alternative non-limiting aspect of this embodiment, about 5-12 volts are directed to the medical device during the electropolishing process; however, other voltage levels can be used. In yet another and/or alternative non-limiting aspect of this embodiment, the medical device is rinsed with water and/or a solvent and allowed to dry to remove polishing solution on the medical device.

In a further and/or alternative non-limiting aspect of the present invention, one or more therapeutic agents can be used with the medical device to facilitate in the success of the medical device and/or treated area. The term "therapeutic agent" includes, but is not limited to, a substance, a pharmaceutical agent, a drug, a biological agent, a veterinary product or drug, and/or analogs or derivatives thereof that are formulated and/or designed to prevent, inhibit and/or treat one or more clinical problems and/or to promote the healing. The one or more layers of therapeutic agent can be applied to the medical device by a variety of techniques (e.g., rolling coating, brush coating, dip coating, flow coating, dip-spin coating, air atomization coating, airless atomization coating, air assisted airless atomization coating, high volume-low pressure air-atomizing spray, flame spray coating, etc.). One non-limiting coating technique is by an ultrasonic mist coating process wherein ultrasonic waves are used to break up the droplet of therapeutic agent and form a mist of very fine droplets. These fine droplets have an average droplet diameter of about 0.1-3 microns. The fine droplet mist facilitates in the formation of a uniform coating thickness and can increase the coverage area on the medical device.

In yet another and/or alternative non-limiting aspect of the invention, the medical device can include a marker material that facilitates enabling the medical device to be properly positioned in a body passageway.

In one non-limiting process for manufacturing a medical device in accordance with the present invention, the process includes the following process steps: 1) forming a novel metal alloy rod or tube; 2) resizing the rod or tube, 3) cleaning and/or pickling the surface of the rod or tube prior to annealing the rod or tube; 4) annealing the rod or tube; and 5) repeating steps 2-4 until the rod or tube has been sized to the desired size. In another and/or alternative non-limiting process for manufacturing a medical device in accordance with the present invention, the process includes the following process steps: 1) forming a novel metal alloy rod or tube; 2) resizing the rod or tube by use of a mandrel and/or plug drawing process, 3) cleaning and/or pickling the surface of the rod or tube prior to annealing the rod or tube; 4) annealing the rod or tube prior to a 60% cross-sectional area size reduction of the rod or tube; 5) repeating steps 2-4 until the rod or tube has been sized to the desired size; 6) cutting and/or etching the rod or tube to at least partially form the medical device; and 7) cleaning and/or electropolishing the medical device. In still another and/or alternative non-limiting process for manufacturing a medical device in accordance with the present invention, the process includes the following process steps: 1) consolidating metal power of the novel metal alloy and/or metal powder of metals that form the novel metal alloy into a tube; 2) resizing the tube one or more times by use of a plug drawing process, 3) cleaning and/or pickling the surface of the tube after each plug drawing process; 4) annealing the tube prior to a 45% cross-sectional area size reduction of the tube; 5) repeating steps 2-4 until the tube has been sized to the desired size; 6) laser cutting the tube to at least partially form the medical device; and 7) cleaning and/or electropolishing the medical device. As can be appreciated, other or additional process steps can be used to form the medical device from a novel metal alloy. In each of the non-limiting processes set forth above, the medical device can be further processed to include 1) a marker material, 2) one or more therapeutic agents and/or 3) one or more polymer coatings.

The use of the novel metal alloy to form all or a portion of a stent results in several advantages over stent formed from other materials. These advantages include, but are not limited to:

The novel metal alloy has increased strength as compared with stainless steel or chromium-cobalt alloys, thus less quantity of novel metal alloy can be used in the stent to achieve similar strengths as compared to stents formed of different metals. As such, the resulting stent can be made smaller and less bulky by use of the novel metal alloy without sacrificing the strength and durability of the stent. The stent can also have a smaller profile, thus can be inserted into smaller areas, openings and/or passageways. The increased strength of the novel metal alloy also results in the increased radial strength of the stent. For instance, the thickness of the walls of the stent and/or the wires used to form the stent can be made thinner and achieve a similar or improved radial strength as compared with thicker walled stents formed of stainless steel or cobalt and chromium alloy.

The novel metal alloy has improved stress-strain properties, bendability properties, elongation properties and/or flexibility properties of the stent as compared with stainless steel or chromium-cobalt alloys, thus resulting in an increase life for the stent. For instance, the stent can be used in regions that subject the stent to repeated bending. Due to the improved physical properties of the stent from the novel metal alloy, the stent has improved resistance to fracturing in such frequent bending environments. These improved physical properties at least in part result from the composition of the novel metal alloy; the grain size of the novel metal alloy; the carbon, oxygen and nitrogen content of the novel metal alloy; and/or the carbon/oxygen ratio of the novel metal alloy.

The novel metal alloy has a reduce the degree of recoil during the crimping and/or expansion of the stent as compared with stainless steel or chromium-cobalt alloys. The stent formed of the novel metal alloy better maintains its crimped form and/or better maintains its expanded form after expansion due to the use of the novel metal alloy. As such, when the stent is to be mounted onto a delivery device when the stent is crimped, the stent better maintains its smaller profile during the insertion of the stent in a body passageway. Also, the stent better maintains its expanded profile after expansion so as to facilitate in the success of the stent in the treatment area.

The novel metal alloy has improved radiopaque properties as compared to standard materials such as stainless steel or cobalt-chromium alloy, thus reducing or eliminating the need for using marker materials on the stent. For instance, the novel metal alloy is at least about 10-20% more radiopaque than stainless steel or cobalt-chromium alloy.

The novel metal alloy is less of an irritant to the body than stainless steel or cobalt-chromium alloy, thus can result in reduced inflammation, faster healing, increased success rates of the stent. When the stent is expanded in a body passageway, some minor damage to the interior of the passageway can occur. When the body begins to heal such minor damage, the body has less adverse reaction to the presence of the novel metal alloy than compared to other metals such as stainless steel or cobalt-chromium alloy.

One non-limiting object of the present invention is the provision of a method and process for forming a novel metal alloy into a medical device.

Another and/or alternative non-limiting object of the present invention is the provision of a method and process for forming a novel metal alloy that inhibits or prevent the formation of micro-cracks during the processing of the alloy into a medical device.

Still another and/or alternative non-limiting object of the present invention is the provision of a method and process for forming a novel metal alloy that inhibits or prevents in the introduction of impurities into the alloy during the processing of the alloy into a medical device.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
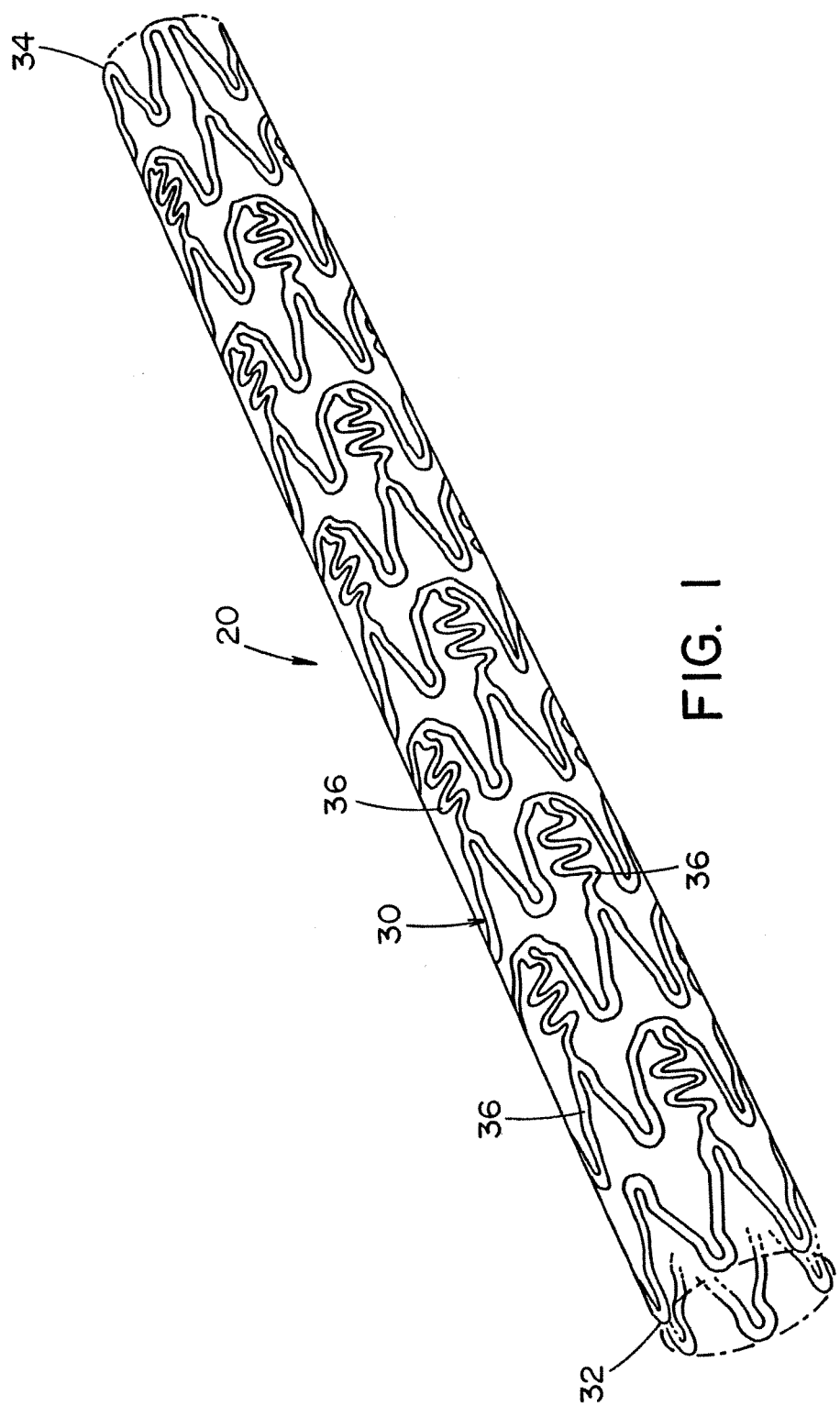
FIG. 1 is a perspective view of a section of a medical device in the form of an unexpanded stent which permits delivery of the stent into a body passageway; and, FIG. 2 is one non-limiting process in accordance with the invention for manufacturing a stent from a molybdenum and rhenium alloy.

Referring now to the drawings wherein the showing is for the purpose of illustrating preferred embodiments of the invention only and not for the purpose of limiting the same, FIG. 1 discloses a medical device in the form of a stent for use in a body passageway. The stent is particularly useful in the cardiovascular field; however, the stent can be used in other medical fields such as, but not limited to, orthopedic field, cardiology field, pulmonology field, urology field, nephrology field, gastrointerology field, gynecology field, otolaryngology field or other surgical fields. Additionally or alternatively, the medical device is not limited to a stent, thus can be in the form of many other medical devices (e.g., a staple, an orthopedic implant, a valve, a vascular implant, a pacemaker, a spinal implant, a guide wire, etc.).

The stent, when used for vascular applications, can be used to addresses various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia or bleeding disorders.

As illustrated in FIG. 1, stent 20 is in the form of an expandable stent that includes at least one tubular shaped body member 30 having a first end 32, a second end 34, and member structures 36 disposed between the first and second ends. As can be appreciated, the stent can be formed of a plurality of body members connected together. Body member 30 has a first outer cross-sectional area or diameter which permits delivery of the body member into a body passageway. The first outer cross-sectional area or diameter of the body member is illustrated as substantially constant along the longitudinal length of the body member. As can be appreciated, the body member can have a varying first outer cross-sectional area or diameter along at least a portion of the longitudinal length of the body member. The body member also has a second expanded outer cross-sectional area or diameter, not shown. The second outer cross-sectional area or diameter typically can vary in size; however, the second outer cross-sectional area or diameter can be non-variable in size. The stent can be expanded in a variety of ways such as by a balloon. A balloon expandable stent is typically pre-mounted or crimped onto an angioplasty balloon catheter. A balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area.

One or more surfaces of the stent can be treated so as to have generally smooth surfaces; however, this is not required. Generally, one or more ends of the stent are treated by filing, buffing, polishing, grinding, coating, and/or the like to remove or reduce the number of rough and/or sharp surfaces; however, this is not required. The smooth surfaces of the ends reduce potential damage to surrounding tissue as the stent is positioned in and/or expanded in a body passageway.

The stent can be at least partially coated with one or more therapeutic agents, not shown. One or more polymers, not shown, can be used in conjunction with the one or more therapeutic agents to 1) facilitate in the bonding of the one or more therapeutic agents to the stent, and/or 2) at least partially control the release of one or more therapeutic agents from the stent.

Figure 2:
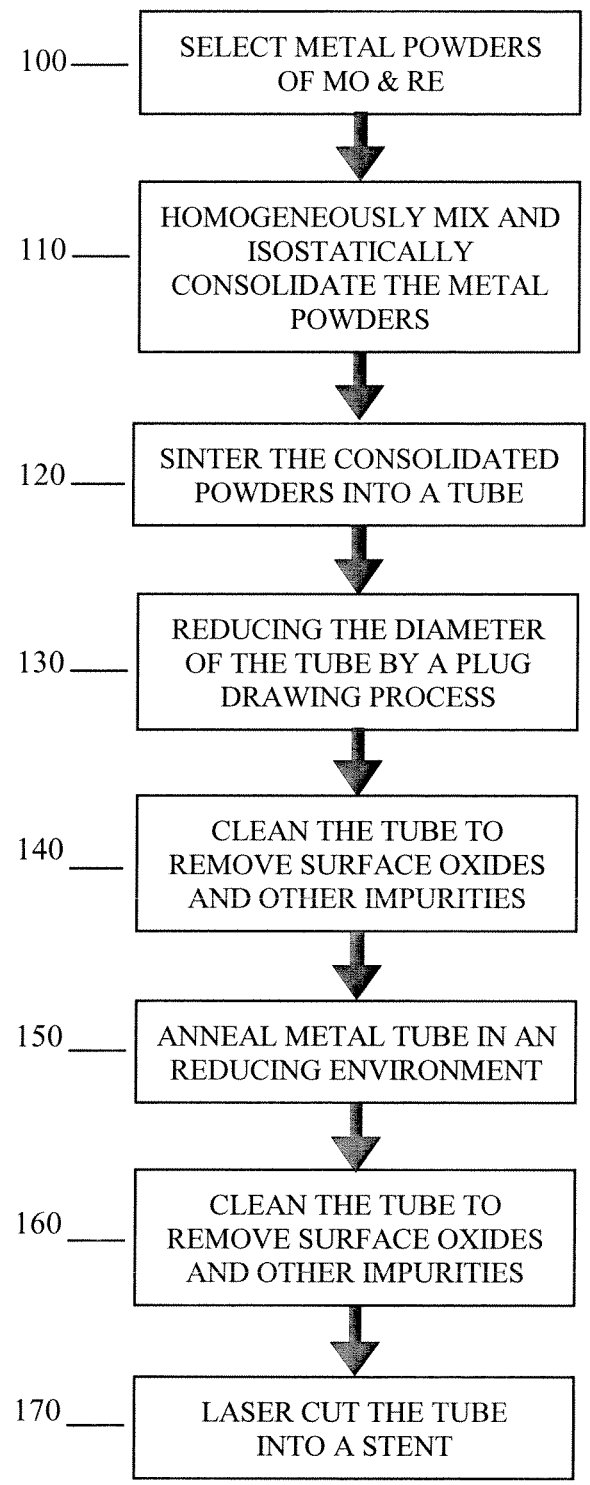

Referring now to FIG. 2, there is illustrated one non-limiting process for forming the stent as illustrated in FIG. 1. The first step to form a stent is to form a tube of a solid solution of molybdenum and rhenium alloy. The tube can be form in a variety of ways. Process step 100 illustrates that metal powders of molybdenum and rhenium are selected to form the tube. The powders of molybdenum and rhenium constitute a majority weight percent of the materials used to form the metal tube. Small amounts of an additional metal such as titanium, yttrium and/or zirconium can also be used; however, this is not required. The purity of the metal powders is selected to minimize the carbon, oxygen and nitrogen content in the metal powder. Typically the carbon content of the metal powders is less than about 150 ppm, the oxygen content of the metal powders is less than about 100 ppm and the nitrogen content of the metal powders is less than about 40 ppm.

After the metal powders have been selected, the metal powders are substantially homogeneously mixed together as illustrated in process step 110. After the metal powders are mixed together, the metal powers are isostatically consolidated to form a tube. One non-limiting isostatic consolidation process is a cold isostatic pressing (CIP) process. The isostatic consolidation process typically occurs in a vacuum environment, an oxygen reducing environment, or in an inert atmosphere. The average density of the metal tube obtained by the isostatic consolidation process is about 80-90% of the final average density of the tube. One non-limiting composition of the tube is a solid solution of about 44-48 weight percent rhenium, about 52-56 weight percent molybdenum, up to about 0.5 weight percent Ti, Y and/or Zr, and no more than about 0.1 weight impurities. After the metal powder has been pressed together, the metal power is sintered to fuse the metal powders together and to form the tube of novel metal alloy. The sinter of the metal powders occurs at a temperature of about 2000-2500° C. for about 5-120 minutes; however, other temperatures and/or sintering time can be used. The sintering of the metal powder typically takes place in an oxygen reducing environment to inhibit or prevent impurities from becoming embedded in the novel metal alloy and/or to further reduce the amount of carbon and/or oxygen in the formed tube. After the sintering process, the tube is formed of a solid solution of the novel metal alloy and has an as-sintered average density of about 90-99% the minimum theoretical density of the novel metal alloy. Typically, the sintered tube has a final average density of about 13-14 gm/cc. The length of the formed tube is typically about 48 inches or less; however, longer lengths can be formed. The average concentricity deviation of the tube is typically about 1-18%. In one non-limiting tube configuration, the tube has an inner diameter of about 0.31 inch (i.e., 0.0755 sq. in. cross-sectional area) plus or minus about 0.002 inch and an outer diameter of about 0.5 inch (i.e., 0.1963 sq. in. cross-sectional area) plus or minus about 0.002 inch. The wall thickness of the tube is about 0.095 inch plus or minus about 0.002 inch. As can be appreciated, this is just one example of many different sized tubes that can be formed.

In another alternative tube forming process, a rod of metal alloy is first formed from one or more ingots of metal alloy. These ingots can be formed by an arc melting process; however, other or additional process can be used to form the metal ingots. The ingots can be formed into a rod by extruding the ingots through a die to form a rod of a desired outer cross-sectional area or diameter. The length of the formed rod is typically about 48 inches or less; however, longer lengths can be formed. After the rod is formed, the rod is hollowed by EDM to form a tube. The inner cross-sectional area or diameter of the hollowed tube is carved to the exact inner cross-sectional area or diameter by a wire EDM process. In one non-limiting tube configuration, the tube has an inner diameter of about 0.2-0.4 inch plus or minus about 0.005 inch and an outer diameter of about 0.4-0.6 inch plus or minus about 0.005 inch. The wall thickness of the tube is about 0.04-0.15 inch plus or minus about 0.005 inch. As can be appreciated, this is just one example of many different sized tubes that can be formed.

The tube can be cleaned and/or polished after the tube has been formed; however, this is not required. The cleaning and/or polishing of the tube is used to remove impurities and/or contaminants from the surfaces of the tube and/or to remove rough areas from the surface of the tube. Impurities and contaminants (e.g., carbon, oxygen, etc.) can become incorporated into the novel metal alloy during the processing of the tube. The inclusion of impurities and contaminants in the novel metal alloy can result in premature micro-cracking of the novel metal alloy and/or the adverse affect on one or more physical properties of the novel metal alloy. The cleaning of the tube can be accomplished by a variety of techniques such as, but not limited to, 1) using a solvent (e.g., acetone, methyl alcohol, etc.) and wiping the novel metal alloy with a Kimwipe or other appropriate towel, and/or 2) by at least partially dipping or immersing the novel metal alloy in a solvent and then ultrasonically cleaning the novel metal alloy.

As can be appreciated, the tube can be cleaned in other or additional ways. The tube, when polished, is generally polished by use of a polishing solution that typically includes an acid solution; however, this is not required. In one non-limiting example, the polishing solution includes sulfuric acid; however, other or additional acids can be used. In one non-limiting polishing solution, the polishing solution can include by volume 60-95% sulfuric acid and 5-40% de-ionized water (DI water). The polishing solution can be increased in temperature during the making of the solution and/or during the polishing procedure. One non-limiting polishing technique that can be used is an electro-polishing technique. The time used to polish the novel metal alloy is dependent on both the size of the tube and the amount of material that needs to be removed from the tube. The tube can be processed by use of a two-step polishing process wherein the novel metal alloy piece is at least partially immersed in the polishing solution for a given period (e.g., 0.1-15 minutes, etc.), rinsed (e.g., DI water, etc.) for a short period of time (e.g., 0.02-1 minute, etc.), and then flipped over and at least partially immersed in the solution again for the same or similar duration as the first time; however, this is not required. The tube can be rinsed (e.g., DI water, etc.) for a period of time (e.g., 0.01-5 minutes, etc.) before rinsing with a solvent (e.g., acetone, methyl alcohol, etc.); however, this is not required. The tube can be dried (e.g., exposure to the atmosphere, maintained in an inert gas environment, etc.) on a clean surface. These polishing procedures can be repeated until the desired amount of polishing of the tube is achieved. Typically, after the tube has been first formed and/or hollowed out, the inner surface (i.e., the inner passageway of the tube) and the outer surface of the tube are polished. The polishing techniques for the inner and outer surfaces of the tube can be the same or different. The inner surface and/or outer surface of the tube is also typically polished at least after one drawing process. As can be appreciated, the inner and/or outer surface of the tube can be polished after each drawing process, and/or prior to each annealing process. A slurry honing polishing process can be used to polishing the inner and/or outer surface of the tube; however, other or additional processes can be used.

After the tube has been formed (e.g., sintering process, extrusion process, etc.), and optionally cleaned, the tube is then drawn through a die one or more times to reduce the inner and outer cross-sectional area or diameter of the tube and the wall thickness of the tube to the desired size. As illustrated in process step 130, the tube is reduced in size by the use of a drawing process such as, but not limited to a plug drawing process. During the drawing process, the tube is heated. During the drawing process, the tube can be protected in a reduced oxygen environment such as, but not limited to, an oxygen reducing environment, or inert environment. One non-limiting oxygen reducing environment includes argon and about 1-10 volume percent hydrogen. When the temperature of the drawing process is less than about 400-450° C., the need to protect the tube from oxygen is significantly diminished. As such, a drawing process that occurs at a temperature below about 400-450° C. can occur in air. At higher temperatures, the tube is drawn in an oxygen reducing environment or an environment. Typically the drawing temperature does not exceed about 500-550° C. A mandrel removal process can be used during the drawing process for the tube to improve the shape and/or uniformity of the drawn tube; however, this is not required. The amount of outer cross-sectional area or diameter draw down of the tube each time the tube is plug drawn is typically no more than about 10-20%. Controlling the degree of draw down facilitates in preventing the formation of micro-cracks during the drawing process. After each drawing process, the tube can be cleaned; however, this is not required. During the drawing process, the inner surface of the tube can be at least partially filled with a close-fitting rod. When a close-fitting rod is used, the metal rod is inserted into the tube prior to the tube being drawn through a die. The close-fitting rod is generally facilitates in maintaining a uniform shape and size of the tube during a drawing process. The close-fitting rod is generally an unalloyed metal rod; however, this is not required. Non-limiting examples of metals that can be used to form the close-fitting rod are tantalum and niobium. When a close-fitting rod is used, the close-fitting rod can be used for each drawing process or for selected drawing processes. Prior to the high temperature annealing of the tube, the close-fitting rod, when used, it removed from the tube. The tube can be heated to facilitate in the removal of the close-fitting rod from the tube; however, this is not required. When the tube is heated to remove the close-fitting rod, the tube is generally no heated above about 1000° C., and typically about 600-800° C.; however, other temperatures can be used. When the tube is heated above about 400-450° C., a vacuum, an oxygen reducing environment or an inert environment is generally used to shield the tube from the atmosphere. As can also be appreciated, a close-fitting tube can also or alternatively be used during the formation of the tube during an extrusion process. Generally after the close-fitting rod is removed from the tube, the inner and/or outer surface of the tube is polished; however, this is not required.

The tube is typically exposed to a nitriding step prior to drawing down the tube. The layer of nitride compound that forms on the surface of the tube after a nitriding process has been found to function as a lubricating layer for the tube as the tube is drawn down to a smaller cross-sectional area or diameter. The nitriding process occurs in a nitrogen containing atmosphere at temperatures exceeding 400° C. Typically the nitriding process is about 5-15 minutes at a temperature of about 450-600° C. The nitrogen atmosphere can be an essentially pure nitrogen atmosphere, a nitrogen-hydrogen mixture, etc.

Prior to the tube being drawn down more than about 35-45% from its original outer cross-sectional area or diameter after the sintering process, the tube is annealed as illustrated in process step 150. If the tube is to be further drawn down after being initially annealed, a subsequent annealing process should be completed prior to the outer cross-sectional area or diameter of the tube being drawn down more than about 35-45% since a previous annealing process. As such, the tube should also be annealed at least once prior to the tube outer cross-sectional area or diameter being drawn down more than about 35-45% since being originally sintered or being previously annealed. This controlled annealing facilitates in preventing the formation of micro-cracks during the drawing process. The annealing process of the tube typically takes place in a vacuum environment, an inert atmosphere, or an oxygen reducing environment (e.g., hydrogen, argon, argon and 1-10% hydrogen, etc.) at a temperature of about 1400-1600° C. for a period of about 5-60 minutes; however, other temperatures and/or times can be used. The use of an oxygen reducing environment during the annealing process can be used to reduce the amount of oxygen in the tube. The chamber in which the tube is annealed should be substantially free of impurities such as, but not limited to, carbon, oxygen, and/or nitrogen. The annealing chamber typically is formed of a material that will not impart impurities to the tube as the tube is being annealed. One non-limiting material that can be used to form the annealing chamber is a molybdenum TZM alloy. The parameters for annealing the tube as the cross-sectional area or diameter and thickness of the tube is changed during the drawing process can remain constant or be varied. It has been found that good grain size characteristics of the tube can be achieved when the annealing parameters are varied during the drawing process. In one non-limiting processing arrangement, the annealing temperature of the tube having a wall thickness of about 0.015-0.05 inch is generally about 1480-1520° C. for a time period of about 5-40 minutes. In another non-limiting processing arrangement, the annealing temperature of the tube having a wall thickness of about 0.008-0.015 inch is generally about 1450-1480° C. for a time period of about 5-60 minutes. In another non-limiting processing arrangement, the annealing temperature of the tube having a wall thickness of about 0.002-0.008 inch is generally about 1400-1450° C. for a time period of about 15-75 minutes. As such, as the wall thickness is reduced, the annealing temperature is correspondingly reduced; however, the times for annealing can be increased. As can be appreciated, the annealing temperatures of the tube can be decreased as the wall thickness decreases, but the annealing times can remain the same or also be reduced as the wall thickness reduces. After each annealing process, the grain size of the metal in the tube should be no greater than 6 ASTM, typically no greater than 7 ASTM, and more typically no greater than about 7.5 ASTM. Grain sizes of 7-14 ASTM can be achieved by the annealing process of the present invention. It is believed that as the annealing temperature is reduced as the wall thickness reduces, small grain sizes can be obtained. The grain size of the metal in the tube should be as uniform as possible. In addition, the sigma phase of the metal in the tube should be as reduced as much as possible. The sigma phase is a spherical, elliptical or tetragonal crystalline shape in the metal alloy. The sigma phase is commonly formed of both rhenium and molybdenum, typically with a larger concentration of rhenium. After the final drawing of the tube, a final annealing of the tube can be done for final strengthening of the tube; however, this is not required. This final annealing process, when used, generally occurs at a temperature of about 1425-1500° C. for about 20-40 minutes; however, other temperatures and/or time periods can be used.

Prior to each annealing process, the tube is cleaned and/or pickled to remove oxides and/or other impurities from the surface of the tube as illustrated in process step 140. Typically the tube is cleaned by first using a solvent (e.g., acetone, methyl alcohol, etc.) and wiping the novel metal alloy with a Kimwipe or other appropriate towel, and/or by at least partially dipping or immersing the tube in a solvent and then ultrasonically cleaning the novel metal alloy. As can be appreciated, the tube can be cleaned other and/or additional ways. After the tube has been cleaned by use of a solvent, the tube is typically further cleaned by use of a pickling process. The pickling process includes the use of one or more acids to remove impurities from the surface of the tube. Non-limiting examples of acids that can be used as the pickling solution include, but are not limited to, nitric acid, acetic acid, sulfuric acid, hydrochloric acid, and/or hydrofluoric acid. The acid solution and acid concentration and time of pickling are selected to remove oxides and other impurities on the tube surface without damaging or over etching the surface of the tube. During the pickling process, the tube is fully or partially immersed in the pickling solution for a sufficient amount of time to remove the impurities from the surface of the tube. After the tube has been pickled, the tube is typically rinsed with a solvent (e.g., acetone, methyl alcohol, etc.) to remove any pickling solution from the tube and then the tube is allowed to dry. The cleaning of the tube prior to the tube being annealed removes impurities and/or other materials from the surfaces of the tube that could become permanently embedded into the tubing during the annealing processes. These imbedded impurities could adversely affect the physical properties of the novel metal alloy as the tube is formed into a medical device, and/or can adversely affect the operation and/or life of the medical device. As can be appreciated, the tube can be again clean and/or pickled after being annealed and prior to be drawn down in the plug drawing process; however, this is not required.

Process steps 130-150 can be repeated as necessary until the tube is drawn down to the desired size. In one non-limiting process, a tube that is originally formed after being sintered has an inner diameter of about 0.31 inch plus or minus about 0.002 inch, an outer diameter of about 0.5 inch plus or minus about 0.002 inch, and a wall thickness of about 0.095 inch plus or minus about 0.002 inch. After the tube has been fully drawn down, the tube has an outer diameter of about 0.070 inch, a wall thickness of about 0.0021-0.00362 inch, and the average concentricity deviation of less than about 10%. Such small sizes for stents which can be successfully used in a vascular system have heretofore not been possible when formed by other types of metal alloys. Typically the wall thickness of stent had to be at least about 0.0027-0.003 inch, or the stent would not have sufficient radial force to maintain the stent in an expanded state after being expanded. The novel metal alloy of the present invention is believed to be able to have a wall thickness of as small as about 0.0015 inch and still have sufficient radial force to maintain a stent in an expanded state after being expanded. As such, when a tube is formed into a stent, the wall thickness of the tube can be drawn down to less than about 0.0027 inch to form a stent. As can be appreciated, this is just one example of many different sized tubes that can be formed by the process of the present invention.

Once the tube has been drawn down to its final size, the tube is typically cleaned (Process Step 140), annealed (Process Step 150) and then again cleaned (Process Step 160). The cleaning step of process step 160 can include merely solvent cleaning, or can also include pickling.

After the tube has been cleaned in process step 160, the tube is then cut into the form of a stent as illustrated in FIG. 1. As can be appreciated, other stent designs can be formed during the cutting process as set forth in process step 170. The cutting of the tube is typically conducted by a laser. The laser that is used to cut the tube is selected so that has a beam strength used to heat the tube can obtain a cutting temperature of at least about 2350° C. Non-limiting examples of lasers that can be used include a pulsed Nd:YAG neodymium-doped yttrium aluminum garnet (Nd:$Y_3Al_5O_{12}$) or $CO_2$ laser. The cutting of the tube by the laser occurs in an oxygen reducing environment such as an argon and 1-10 percent by volume hydrogen environment; however, a vacuum environment, an inert environment, or another type of oxygen reducing environment can be used. During the cutting of the tube, the tube is typically stabilized so as to inhibit or prevent vibration of the tube during the cutting process, which vibrations can result in the formation of micro-cracks in the tube as the tube is cut. The tube is typically stabilized by an apparatus formed of molybdenum, rhenium, tungsten, molybdenum TZM alloy, ceramic, etc. so as to not introduce contaminates to the tube during the cutting process; however, this is not required. The average amplitude of vibration during the cutting of the tube is typically no more than about 50% the wall thickness of the tube. As such, for a tube having a wall thickness of about 0.0024 inch, the average amplitude of vibration of the tube during the cutting process is no more than about 0.0012 inch.

The formed stent typically has a tensile elongation of about 25-35%, an average density of about 13.4-14 gm/cc., an average yield strength of at least about 100 (ksi), an average ultimate tensile strength of about 150-310 UTS (ksi), and an average Vickers hardness of 372-653 (i.e., an average Rockwell A Hardness of about 70-80 at 77° F., an average Rockwell C Hardness of about 39-58 at 77° F. The solid or homogeneous solution of the metal alloy that is used to form the stent has the unique characteristics of purity, ductility, grain size, tensile elongation, yield strength and ultimate tensile strength that permits 1) the metal alloy to be fabricated into the stent from the tube without creating microcracks which are detrimental to the stent properties, and 2) the manufacture of a stent that has improved physical properties over stents formed from different materials.

After the stent has been cut, the stent can be further processed; however, this is not required. The one or more processes can include, but are not limited to, 1) electropolishing the stent, 2) treating one or more surfaces of the stent to created generally smooth surfaces and/or other types of surfaces (e.g., filing, buffing, polishing, grinding, coating, nitriding, etc.), 3) at least partially coating the stent with one or more therapeutic agents, 4) at least partially coating the stent with one or more polymers, 5) forming one or more surface structures and/or micro-structures on one or more portions of the stent, 6) inserting one or more markers on one or more portions of the stent, and/or 7) straightening process for the stent. For instance, the stent can be nitrided to obtain differing surface characteristics of the stent and/or to inhibit oxidation of the surface of the stent; however, this is not required. The stent can be electropolished to fully or selectively expose one or more surface regions of the stent; however, this is not required. The stent is typically straightened in a roll straightener and/or other type of device to obtain the designed shape of the stent; however, this is not required. After the stent has been straightened, the stent can be centerless ground to obtain the desired dimensions of the stent; however, this is not required. The stent can be polished after the grinding process; however, this is not required.

The invention has been specifically described with respect to the formation of a stent. As can be appreciated, other types of medical devices can be formed by use of one or more of the novel processing step of the present invention. For example, the novel metal allow can be drawn using one or more of the processes of the present invention to form a thin wire for use as a suture, a guide wire, a stent, or the like.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method for forming an expandable medical device comprising the steps of:
   a) forming a rod or tube having a surface and an original outer cross-sectional area, said rod or tube being formed of a metal alloy, said metal alloy including two or more metals selected from the group consisting of calcium, chromium, cobalt, copper, gold, iron, lead, magnesium, molybdenum, nickel, niobium, platinum, rare earth metals, rhenium, silver, tantalum, titanium, tungsten, yttrium, zinc, and zirconium, said metal alloy including at least one metal selected from the group consisting of molybdenum, rhenium, tantalum, tungsten;
   b) drawing down said outer cross-sectional area of said rod or tube to a first drawn down cross-sectional area by a reducing mechanism, said rod or tube being drawn down at least once to obtain said first drawn down cross-sectional area, said outer cross-sectional area being reduced by no more than about 25% during each drawing down process;
   c) annealing said rod or tube during a first annealing step prior to said rod or tube having said original outer cross-sectional area drawn down by more than about 60%, said step of annealing performed at a first annealing temperature when said rod or tube is at said first drawn down cross-sectional area;
   d) drawing down said cross-sectional area of said rod or tube from said first drawn down cross-sectional area to a second drawn down cross-sectional area by the reducing mechanism after said rod or tube has been annealed, said second drawn down cross-sectional area smaller than said first drawn down cross-sectional area, said rod or tube being drawn down at least once to obtain said second drawn down cross-sectional area, said outer cross-sectional area reduced by no more than about 25% during each drawing down process;
   e) annealing said rod or tube during a second annealing step prior to said rod or tube having said first drawn down cross-sectional area being drawn down by more than about 60%, said step of annealing performed at a second annealing temperature when said rod or tube is at said second drawn down cross-sectional area, said second annealing temperature lower temperature than said first annealing temperature;
   f) controlling an atmosphere about said rod or tube during said steps of drawing and annealing so that said metal alloy of said rod or tube after final drawing and annealing steps includes less than about 30 ppm nitrogen, less than about 200 ppm carbon, and less than about 150 ppm oxygen; and,
   g) repeating steps d, e and f until said tube is at a desired thickness.

2. The method as defined in claim 1, wherein said step of forming said rod or tube includes a process of isostatically pressing metal powder together and subsequently sintering said metal power to form said rod or tube in a controlled atmosphere, said rod or tube having an average density of about 0.7-0.95 a minimum theoretical density of said metal alloy, said rod or tube have an average density of about 12-14 gm/cc, said controlled atmosphere including an inert atmosphere, an oxygen reducing atmosphere, or a vacuum.

3. The method as defined in claim 2, wherein said tube is formed by gun drilling, EDM cutting, and combinations thereof a passageway at least partially through a longitudinal length of said rod.

4. The method as defined in claim 1, wherein said step of forming said rod or tube includes a) forming an ingot of metal, b) extruding said ingot through a die to form a rod, c) hollowing out said rod to form a passageway at least partially through a longitudinal length of said rod, and d) polishing a surface of said passageway.

5. The method as defined in claim 4, wherein said step of hollowing includes gun drilling, EDM cutting, and combinations thereof said rod to form said passageway.

6. The method as defined in claim 1, wherein said metal alloy includes rhenium and molybdenum.

7. The method as defined in claim 6, wherein said metal alloy includes about 40-55 weight percent rhenium, about 45-60 weight percent molybdenum, and up to about 5 weight percent additional metal, said additional metal including one or more metals selected from the group consisting of titanium, yttrium, and zirconium.

8. The method as defined in claim 7, including the step of protecting said rod or tube from oxygen when said rod or tube is exposed to temperatures of greater than about 400-500° C.

9. The method as defined in claim 7, wherein said step of drawing down said cross-sectional area of said rod or tube by a reducing mechanism that reduces said cross-sectional area by less than about 20% each time said rod or tube is processed by said reducing mechanism.

10. The method as defined in claim 1, including the step of nitriding said rod or tube to form a nitride layer on said rod or tube prior to at least one drawing down step, said step of nitriding including a) exposing at least a portion of said rod or tube to a nitriding gas that includes nitrogen, nitrogen and hydrogen, and combinations thereof, and b) exposing at least a portion of said rod or tube to a nitriding gas at a temperature of at least about 400° C. for at least about 1 minute.

11. The method as defined in claim 7, including the step of nitriding said rod or tube to form a nitride layer on said rod or tube prior to at least one drawing down step, said step of nitriding including a) exposing at least a portion of said rod or tube to a nitriding gas that includes nitrogen, nitrogen and hydrogen, and combinations thereof, and b) exposing at least a portion of said rod or tube to a nitriding gas at a temperature of at least about 400° C. for at least about 1 minute.

12. The method as defined in claim 10, including the step of removing said nitride layer on said rod or tube prior to annealing said rod or tube.

13. The method as defined in claim 11, including the step of removing said nitride layer on said rod or tube prior to annealing said rod or tube.

14. The method as defined in claim 1, including the step of protecting said rod or tube from oxygen when said rod or tube is exposed to temperatures of greater than about 400-500° C.

15. The method as defined in claim 13, including the step of protecting said rod or tube from oxygen when said rod or tube is exposed to temperatures of greater than about 400-500° C.

16. The method as defined in claim 1, wherein said step of drawing down said cross-sectional area of said rod or tube by a reducing mechanism that reduces said cross-sectional area by less than about 20% each time said rod or tube is processed by said reducing mechanism.

17. The method as defined in claim 15, wherein said step of drawing down said cross-sectional area of said rod or tube by a reducing mechanism that reduces said cross-sectional area by less than about 20% each time said rod or tube is processed by said reducing mechanism.

18. The method as defined in claim 16, wherein said step of drawing down includes the step of inserting a close-fitting rod in a passageway of said tube prior to using said reducing mechanism on said tube, said close-fitting rod formed of tantalum and niobium.

19. The method as defined in claim 17, wherein said step of drawing down includes the step of inserting a close-fitting rod in a passageway of said tube prior to using said reducing mechanism on said tube, said close-fitting rod formed of tantalum and niobium.

20. The method as defined in claim 1, wherein said first step of annealing said rod or tube includes annealing said rod or tube at said first annealing temperature of at least about 1480° C. for a time period of at least about 5 minutes when said rod or tube has wall thickness of greater than about 0.015 inch, said second step of annealing said rod or tube includes annealing said rod or tube at said second annealing temperature of at least about 1450° C. for a time period of at least about 5 minutes when said rod or tube has all thickness of about 0.008-0.015 inch, and including the further step of annealing said rod or tube a third time at a third annealing temperature of less than about 1450° C. for a time period of at least about 5 minutes when said rod or tube has wall thickness of less than about 0.008 inch.

21. The method as defined in claim 17, wherein said first step of annealing said rod or tube includes annealing said rod or tube at said first annealing temperature of at least about 1480° C. for a time period of at least about 5 minutes when said rod or tube has wall thickness of greater than about 0.015 inch, said second step of annealing said rod or tube includes annealing said rod or tube at said second annealing temperature of at least about 1450° C. for a time period of at least about 5 minutes when said rod or tube has wall thickness of about 0.008-0.015 inch, and including the further step of annealing said rod or tube a third time at a third annealing temperature of less than about 1450° C. for a time period of at least about 5 minutes when said rod or tube has wall thickness of less than about 0.008 inch.

22. The method as defined in claim 1, wherein said tube having a grain size after said final drawing down step of up to 14 ASTM.

23. The method as defined in claim 21, wherein said tube having a gain size after said final drawing down step of up to 14 ASTM.

24. The method as defined in claim 1, wherein said medical device is a stent.

25. The method as defined in claim 23, wherein said medical device is a stent.

26. The method as defined in claim 24, including the step of cutting said tube to at least partially form said stent.

27. The method as defined in claim 25, including the step of cutting said tube to at least partially form said stent.

28. The method as defined in claim 26, wherein said step of cutting is at least partially by a laser, said laser cutting of said tube at least partially conducted in a vacuum or an inert atmosphere.

29. The method as defined in claim 27, wherein said step of cutting is at least partially by a laser, said laser cutting of said tube at east partially conducted in a vacuum or an inert atmosphere.

30. The method as defined in claim 26, including the step of electropolishing said stent after said cutting step.

31. The method as defined in claim 29, including the step of electropolishing said stent after said cutting step.

32. The method as defined in claim 1, including the step of using a lubricant during said drawing down of said tube, said lubricant including a molybdenum containing lubricant.

33. The method as defined in claim 31, including the step of using a lubricant during said drawing down of said tube, said lubricant including a molybdenum containing lubricant.

34. The method as defined in claim 1, wherein said first step of annealing said rod or tube includes annealing said rod or tube at said first annealing temperature of at least about 1480° C. for a time period of at least about 5 minutes when said rod or tube has wall thickness of greater than about 0.015 inch, said second step of annealing said rod or tube includes annealing said rod or tube at said second annealing temperature of at least about 1450° C. for a time period of at least about 5 minutes when said rod or tube has wall thickness of about 0.008-0.015 inch, and including the further step of annealing said rod or tube a third time at a third annealing temperature of less than about 1450° C. for a time period of at least about 5 minutes when said rod or tube has wall thickness of less than about 0.008 inch.

35. The method as defined in claim 1, wherein said first step of annealing said rod or tube includes annealing said rod or tube at said first annealing temperature of at least about 1480-1520° C. for a time period of about 5-40 minutes when said rod or tube has wall thickness of greater than about 0.015 inch, said second step of annealing said rod or tube includes annealing said rod or tube at said second annealing temperature of about 1450-1480° C. for a time period of about 5-60 minutes when said rod or tube has wall thickness of about 0.008-0.015 inch, and including the further step of annealing said rod or tube a third time at a third annealing temperature of about 1400-1450° C. for a time period of about 15-75 minutes when said rod or tube has wall thickness of less than about 0.008 inch.

* * * * *